United States Patent
Delfourne et al.

(10) Patent No.: US 6,809,096 B1
(45) Date of Patent: Oct. 26, 2004

(54) PHENANTHROLINE-7-ONE DERIVATIVES AND THEIR THERAPEUTIC USES

(75) Inventors: Evelyne Delfourne, Pollestres (FR); Francis Darro, Brussels (BE); Jean Bastide, Perpignan (FR); Robert Kiss, Wauthier-Braine (BE); Armand Frydman, Verrieres le Buisson (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 10/049,511
(22) PCT Filed: Aug. 11, 2000
(86) PCT No.: PCT/FR00/02313
§ 371 (c)(1),
(2), (4) Date: Feb. 13, 2002
(87) PCT Pub. No.: WO01/12632
PCT Pub. Date: Feb. 22, 2001

(30) Foreign Application Priority Data

Aug. 13, 1999 (FR) ............................... 99 10493

(51) Int. Cl.$^7$ .................. C07D 471/16; A61K 31/5355; A61K 31/4375; A61P 35/00
(52) U.S. Cl. ...................... 514/232.8; 514/287; 546/64; 546/81; 544/125; 544/126
(58) Field of Search .................... 546/64, 81; 544/125, 544/126; 514/287, 232.8

(56) References Cited

U.S. PATENT DOCUMENTS 5,182,287 A    1/1993 Gunawardana et al. ..... 514/260

OTHER PUBLICATIONS

Matsumato et al. (Tetrahedron Letters 41 (2000) 1667–1670, issue of Mar. 4, 2000).*

Tetrahedron Letters, Matsumoto et al., "Mechanism of Action Studies of Cytotoxic Marine Alkaloids: Ascididemin Exhibits Thiol–Dependent Oxidative DNA Cleavage", 2000, pp. 1667–1670.

* cited by examiner

Primary Examiner—Mark L. Berch
Assistant Examiner—Kahsay Habte
(74) Attorney, Agent, or Firm—Young & Thompson

(57) ABSTRACT

A pharmaceutical composition including an efficient amount of a compound selected among the compounds of formulae (I) and (Ia). The compounds have interesting cytotoxic properties leading to a therapeutic use as antitumoral medicines.

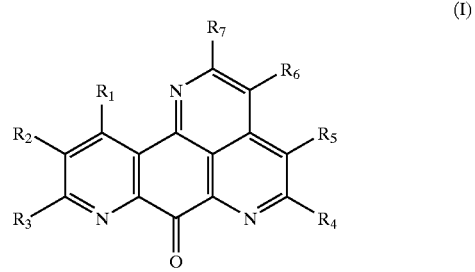

(I)

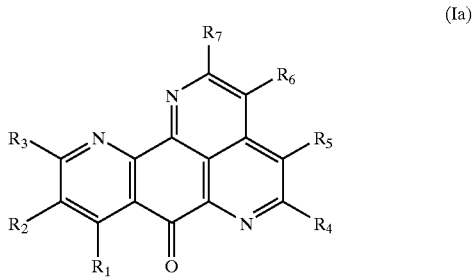

(Ia)

13 Claims, No Drawings

PHENANTHROLINE-7-ONE DERIVATIVES AND THEIR THERAPEUTIC USES

The present invention relates to pharmaceutical compositions based on polyaromatic compounds of use in particular as antitumour medicaments.

In 1999, cytotoxic treatments (chemotherapy) used to reduce the size of cancerous tumours, to suppress the development of the tumour process or indeed even, in still too few cases, to eliminate clumps of cancer cells and the risk of metastases, combine chemical substances which have been recently introduced with to others which have been used for several decades. For example, 5-fluorouracil (5-FU), recognized for nearly 40 years as one of the most active treatments for colorectal cancer, can be replaced by one or other of the specific inhibitors of topoisomerase I (irinotecan or topotecan) when the tumour is no longer sensitive to 5-FU. More generally, the therapeutic arsenal available for treating colorectal tumours will also be enriched with the availability of oxaliplatin, novel in situ "donors" of 5-FU or selective inhibitors of thymidylate synthetase. This coexistence is not limited to the treatment of colorectal cancers since, in addition, the chemotherapy of breast, ovarian and lung cancers now makes wide use of the family of taxane derivatives (paclitaxel, docetaxel). The need for more effective and better tolerated treatments, thus improving the survival and the quality of life of the patients, is imperative since, still taking the example of colorectal tumours, it has been estimated (S. L. Parker, T. Tong, S. Bolden et al., CA Cancer J. Clin., 1997) that, in the United States alone, over 131 000 new cases were diagnosed in 1997, 54 000 of which were responsible for the death of the patient. It is the awareness of this situation which has prompted the inventors to focus their attention on a family of polyaromatic compounds which have not yet been studied to any great extent, identified in the Ascidia of warm seas, in order to develop a novel medicinal chemistry intended to select synthetic compounds resulting from chemical design/modulation research which possess a significant cytotoxic activity at the therapeutic level.

The seas and oceans which cover more than 70% of the surface of the planet harbour marine plants and sponges, which living species, under gradual systematic pharmacognosic, have been shown to be able to contain complex alkaloids exhibiting advantageous pharmacological properties. For example, the sponges *Cryptotheca crypta* and *Halichondria okadai* have formed the subject of in-depth studies since the discovery of the presence, in their cells, of cytarabine or of halichondrin B. It is the same for the tunicates, since the isolation of aplidine from the tunicate *Aplidium albicans*, which lives in the Balearic Islands (Spain). Alkaloids with a tetrahydroisoquinolone structure have been isolated from the ascidian *Ecteinascidia turbinata*. Among these, ecteinascidin-743 has formed the subject of in-depth preclinical studies (E. Igbicka et al., NCI-EORTC symposium, 1998; Abst. 130, p. 34) and of clinical trials intended to define its therapeutic potential as anticancer medicament (A. Bowman et al., NCI-EORTC symposium, 1998; Abst. 452, p. 118; M. Villanova-Calero et al., NCI-EORTC symposium, 1998; Abst. 453, p. 118; M. J. X. Hillebrand et al., NCI-EORTC symposium; 1998; Abst. 455, p. 119; E. Citkovic et al., NCI-EORTC symposium, 1998; Abst. 456, p. 119). Novel pentacyclic acridine derivatives have also formed the subject of pharmacochemical studies (D. J. Hagan et al., J. Chem. Soc., Perkin Transf., 1997; 1: 2739–2746).

Other natural alkaloid of marine origin, ascididemin, has been extracted from the tunicate Didemnum sp. (J. Kobayashi et al., Tetrahedron Lett., 1988; 29: 1177–80) and from the ascidian *Cystodytes dellechiajei* (I. Bonnard et al., Anti-cancer Drug Design, 1995; 10: 333–46). Ascididemin has antiproliferative properties demonstrated on the model of murine leukaemia (P388 or L1210 lines) and described by F. J. Schmitz et al. (J. Org. Chem. 1991; 56: 804–8), B. Lindsay et al. (Bioorg. Med. Chem. Lett., 1995; 5: 739–42) and J. Kobayashi et al. (Tetrahedron Lett., 1988; 29: 1177–80), and on the model of human leukaemia as described by I. Bonnard et al. (Anti-cancer Drug Design, 1995; 10: 333–46). Mention may also be made of 2-bromoleptoclinidone, isolated from the ascidian Leptoclinides sp. by S. J. Bloor et al. (J. Am. Chem. Soc., 1987; 109: 6134–6) and synthesized by F. Bracher et al. (Heterocycles, 1989; 29: 2093–95) and then by M. E. Jung et al. (Heterocycles, 1994; 39; 2: 767–778). 2-Bromoleptoclinidone exhibits cytotoxicity with respect to the leukaemia cell model with an $ED_{50}$ of 0.4 μg/ml. The cytotoxic properties were confirmed by F. Bracher (Pharmazie, 1997; 52: 57–60), both in vitro, on sixty tumour cell lines in culture, and in vivo, on models of xenografts of human tumour cell lines (colon tumours SW-620 and HTC116, renal tumour A498 and melanoma LOX IM VI) implanted in mice.

Other compounds derived from ascididemin, such as 11-hydroxyascididemin, 11-methoxyascididemin, 11-phenylascididemin, 11-nitrophenylascididemin, 1-nitroascididemin, 3-nitroascididemin and neocalliactine, have been described chemically by various groups, such as those of F. J. Schmitz (J. Org. Chem., 1991; 56: 804–8) and Y. Kitahara et al. (Heterocycles, 1993; 36: 943–46; Tetrahedron Lett., 1997; 53, 17029–38), G. Gellerman et al. (Tetrahedron Lett., 1993; 34: 1827–30), S. Nakahara et al., (Heterocycles, 1993; 36: 1139–44) and I. Spector et al. (U.S. Pat. No. 5,432,172).

Meridine is another natural alkaloid extracted from the ascidian *Amphicarpa meridiana* or from the marine sponge Corticum sp. Meridine was isolated by F. J. Schmitz et al. (J. Org. Chem., 1991; 56: 804–808) and then described for its antiproliferative properties on a model of murine leukaemia (P388) and its antifungal properties in U.S. Pat. No. 5,182,287 (Gunawardana et al. of 23 Jan. 1993). Its cytotoxic properties on two human cell lines, colon cancer cells (HT-29) and lung carcinoma cells (A549), were reported by R. E. Longley et al. (J. of Nat. Products, 1993; 56: 915–920).

Mention may also be made, among these compounds, of cystodamine, a pentacyclic alkaloid isolated from the ascidian *Cystodytes dellechiajei* by N. Bontemps et al. (Tetrahedron Lett., 1994; 35: 7023–7026), which exhibits cytotoxic activity with respect to human leukaemia lymphoblasts.

A subject-matter of the present invention is compounds of general formula I and Ia

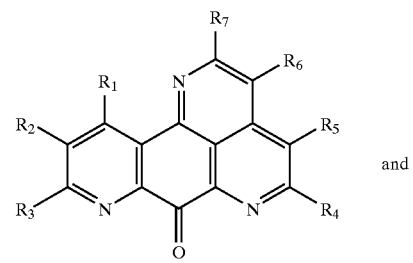

Formula I and

Formula Ia

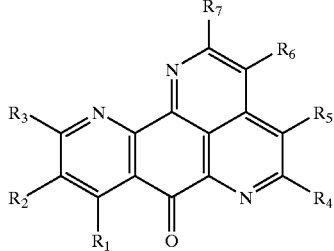

in which:

R$_1$, R$_2$, R$_3$, R$_4$ and R$_5$ are selected from hydrogen, halogens, C$_1$–C$_6$ alkyl groups, hydroxyl, —CHO, —OR$_8$, —COOH, —CN, —CO$_2$R$_8$, —CONHR$_8$, —CONR$_8$R$_9$, —NH$_2$, —NHR$_8$, —N(R$_8$)$_2$, —NH—CH$_2$—CH$_2$—N(CH$_3$)$_2$, —NH—CH$_2$—CH$_2$—Cl, —NHCOR$_8$, morpholino, nitro, SO$_3$H,

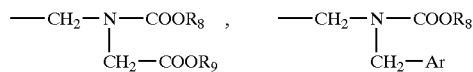

R$_8$ and R$_9$ being selected from C$_1$–C$_6$ alkyl groups and phenyl(C$_1$–C$_4$)alkyl groups and Ar being a C$_6$–C$_{14}$ aryl group, R$_6$ is selected from hydrogen, halogens, C$_1$–C$_6$ alkyl or —(CH$_2$)$_n$R$_{10}$ groups with R$_{10}$ being selected from halogens or —OH, (C$_1$–C$_6$)alkoxy or —O—CO—(C$_1$–C$_6$)alkyl groups and n between 1 and 6, —CN, —CO$_2$Et or —COR$_{11}$ groups with R$_{11}$ being selected from C$_1$–C$_6$ and phenyl(C$_1$–C$_4$)alkyl groups, and —NR$_{12}$R$_{13}$ groups with R$_{12}$ and R$_{13}$ selected, independently of one another, from hydrogen or C$_1$–C$_6$ alkyl, phenyl(C$_1$–C$_4$)alkyl or —(CH$_2$)$_n$R$_{14}$ groups with R$_{14}$ being selected from halogens or (C$_1$–C$_6$)alkoxy and —N(CH$_3$)$_2$ groups and n between 1 and 6, R—R$_7$ is selected from hydrogen, groups of type (C$_1$–C$_6$)alkyl, phenyl(C$_1$–C$_4$)alkyl, —NR$_{15}$R$_{16}$ with R$_{15}$ and R$_{16}$ selected, independently of one another, from hydrogen, groups of type C$_1$–C$_6$ alkyl and phenyl(C$_1$–C$_4$)alkyl and —(CH$_2$)$_n$R$_{17}$, with R$_{17}$ selected from hydrogen, halogens or —OH or (C$_1$–C$_6$)alkoxy groups and n between 1 and 6, and the addition salts of these compounds with pharmaceutically acceptable acids.

A specific group of compounds of the formula I and/or Ia is those in which:

R$_1$, R$_2$, R$_3$, R$_4$ and R$_5$ are selected from hydrogen, halogens, C$_1$–C$_6$ alkyl groups, hydroxyl, —CHO, —OR$_8$, —COOH, —CN, —CO$_2$R$_8$, —CONHR$_8$, —CONR$_8$R$_9$, —NH$_2$, —NHR$_8$, —N(R$_8$)$_2$, —NH—CH$_2$—CH$_2$—N(CH$_3$)$_2$, —NHCOR$_8$, morpholino, nitro, SO$_3$H,

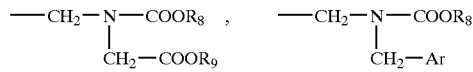

R$_8$ and R$_9$ being selected from C$_1$–C$_6$ alkyl groups and Ar being a C$_6$–C$_{14}$ aryl group.

The subject-matter of the present invention is more particularly the compounds selected from the compounds of formula (I) and of formula (Ia) in which R$_1$, R$_2$, R$_3$, R$_4$ and R$_5$ are selected from hydrogen, halogens, C$_1$–C$_6$ alkyl groups, hydroxyl, —OR$_8$, NO$_2$, —NH$_2$, —NHR$_8$, —NH(R$_8$)$_2$, —NH—CH$_2$—CH$_2$—N(CH$_3$)$_2$, —NH—CH$_2$—CH$_2$—Cl, —NHCOR$_8$, R$_8$ being selected from C$_1$–C$_6$ alkyl groups, R$_6$ is selected from hydrogen, —(CH$_2$)$_n$R$_{10}$ groups, with R$_{10}$ being selected from halogens, the —O—CO—CH$_3$ group, C$_1$–C$_6$ alkyl groups and N(R$_{12}$R$_{13}$) groups with R$_{12}$ and R$_{13}$ selected, independently of one another, from hydrogen or C$_1$–C$_6$ alkyl, benzyl or —(CH$_2$)$_n$R$_{14}$ groups, with R$_{14}$ being selected from halogens or (C$_1$–C$_6$)alkoxy and —N(CH$_3$)$_2$ groups and n between 1 and 6, R$_7$ selected from hydrogen or groups of type (C$_1$–C$_6$) alkyl, benzyl, —N(R$_{15}$R$_{16}$) with R$_{15}$ and R$_{16}$ selected from hydrogen, groups of type C$_1$–C$_6$ alkyl and benzyl, and —(CH$_2$)$_n$R$_{17}$, with R$_{17}$ selected from hydrogen, halogens or —OH or (C$_1$–C$_6$)alkoxy groups and n between 1 and 6, and the addition salts of these compounds with pharmaceutically acceptable acids.

A group of preferred compounds is that composed of the compounds of formula I and Ia in which at least one of the R$_1$, R$_2$, R$_3$, R$_4$ and R$_5$ groups is an OR$_8$ group.

The "addition salts with pharmaceutically acceptable acids" denote the salts which give the biological properties of the free bases without having an undesirable action. These salts can in particular be those formed with inorganic acids, such as hydrochloric acid, hydrobromic acid, sulphuric acid, nitric acid or phosphoric acid; metal acid salts, such as disodium orthophosphate and monopotassium sulphate, and organic acids.

Generally, the compounds of formula (I) and (Ia) can be obtained by a process which consists in:

a) reacting, according to a hetero Diels-Alder reaction, a quinolinedione of formula:

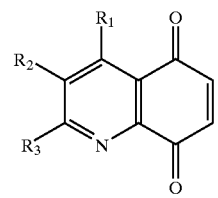

IV and an azadiene of formula:

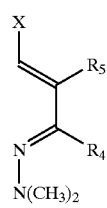

V where X=CH$_3$, in order to obtain a mixture of compounds

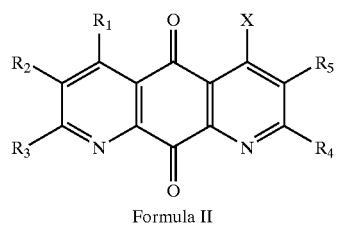

Formula II

+

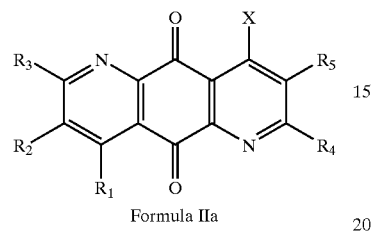

Formula IIa b) in optionally separating the compounds of formulae II and IIa, c₁) subsequently reacting a compound of formulae II and/or IIa with dimethylformamide dimethyl acetal, in order to obtain an enamine of formula:

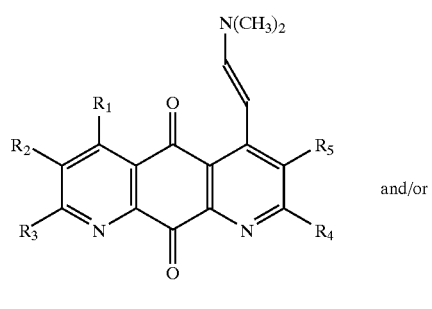

Formula III and/or

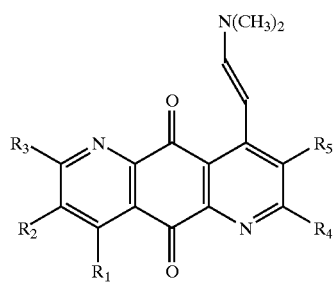

Formula IIIa then functionalizing the enamines, in order to introduce the $R_6$ and/or $R_7$ substituents, and cyclizing, in order to obtain the compounds of formulae I and/or Ia, or c₂) functionalizing and cyclizing at the same time, in order to obtain the compounds of formulae I and/or Ia, d) optionally separating the compounds of formulae I and Ia.

In an alternative form, the compounds of formulae I or Ia in which $R_6$ and $R_7$ are hydrogens can be obtained by a process which consists in:

a) reacting:

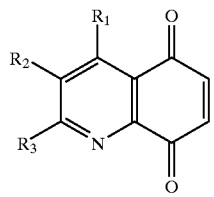

IV and an azadiene of formula

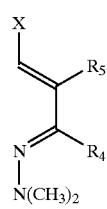

V where X=CH₂—CH₂—NHBoc,
in order to obtain a mixture of compounds

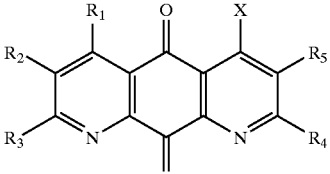

Formula II

+

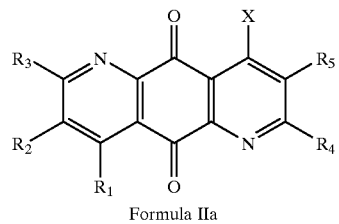

Formula IIa b) optionally separating the compounds of formulae II and IIa, c) cyclizing a compound of formulae II and/or IIa, in order to obtain a compound of formulae I and/or Ia, d) optionally separating the compounds of formulae I or Ia.

The reaction for cyclization of the compounds of formulae III and IIIa can be obtained under hot conditions in the presence of NH₄Cl in an appropriate solvent.

When X=CH₂—CH₂—NHBoc, the compounds of formulae I and Ia are obtained directly in the presence of NaHCO₃ in trifluoroacetic acid medium from the compounds of formulae II and IIa.

The functionalization for the introduction of the $R_6$ substituent can be obtained with derived reactants, such as R—COCl, ClCN, ClCO₂Et, ClCH₂OR, FClO₃ or CH₂=N⁺(CH₃)₂I⁻ (in CH₃COOH).

The functionalization for the introduction of an $R_7$ substituent can be obtained by a Mannich reaction with an aldehyde of formula R₇—CHO.

In this case, the simultaneous cyclization can be obtained in the presence of excess ammonium chloride in acetic acid.

An example of substituted azadiene can be prepared according to the following scheme:

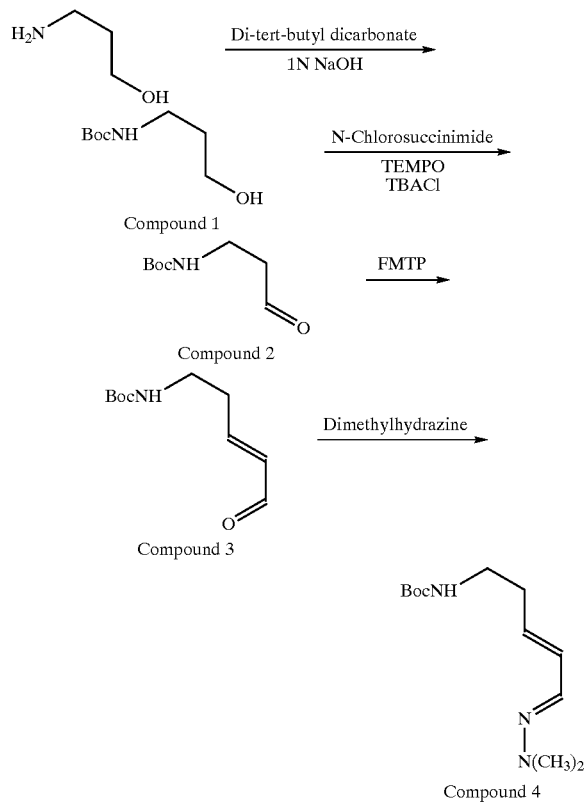

TEMPO = tetramethyl-1-piperidinyloxy, free radical
TBACl = tetrabutylammonium chloride
FMTP = formylmethylenetriphenylphosphorane The following examples illustrate the preparation of the compounds of formulae (I) and (Ia).

A—Preparation of the Azadiene (Compound 4)

A-1—Synthesis of N-BOC-1-amino-2-hydroxypropane is (Compound 1)

4.2 g (29.7 mmol) of di-tert-butyl dicarbonate are added at 0° C. to a solution of 2 ml (27 mmol) of 3-amino-1-propanol in a mixture of 60 ml of dioxane, 30 ml of water and 30 ml of 1N NaOH. The reaction mixture is kept stirred at ambient temperature overnight and then it is acidified to pH 1 using concentrated HCl. After several extractions (3 times 50 ml) with ethyl acetate (AcOEt), the organic phases are dried over MgSO$_4$ and then concentrated on a rotary evaporator to give 4 g of the expected product in the form of a yellow oil.

Yield: 85%.

$^1$H NMR (CDCl$_3$): 1.25 (s, 9H); 2.50 (m, 2H); 3.05 (m, 2H); 3.45 (m, 2H); 5.40 (broad s, 1H).

A-2—Synthesis of N-BOC-3-aminopropanal (Compound 2)

18 g (103 mmol) of Compound 1, 1.62 g (10.4 mmol) of TEMPO (tetramethyl-1-piperidinyloxy, free radical), 2.9 g (10.45 mmol) of tetrabutylammonium chloride and 21 g (75.5 mmol) of N-chlorosuccinimide are suspended in 351 ml of NaHCO$_3$/K$_2$CO$_3$ (0.5N/0.05N) and 351 ml of CHCl$_3$. The reaction mixture is vigorously stirred for 2 hours. The organic phase is separated by settling, dried over MgSO$_4$ and then concentrated on a rotary evaporator to give the expected aldehyde in the form of a light orange oil.

Yield: 100%

$^1$H NMR (CDCl$_3$): 1.35 (s, 9H); 2.44 (d, 2H, J=6.8 Hz); 3.21 (m, 2H); 4.90 (broad s, 1H); 6.04 (dd, 1H, J=8 and 15.6 Hz); 6.74 (td, 1H, J=6.8 and 15.6 Hz); 9.39 (d, 1H, J=8 Hz).

A-3—Synthesis of N-BOC-5-amino-2-penten-1-al (Compound 3)

11 g (66.7 mmol) of Compound 2 and 24.3 g (80 mmol) of formylmethylenetriphenylphosphorane (FMTP) are dissolved in 350 ml of benzene and then the reaction mixture is brought to reflux for 9 hours. After evaporating the solvent on a rotary evaporator, the residue is filtered a first time through silica [(1/1 CHCl$_3$/heptane) then CHCl$_3$] to remove the triphenyl-phosphine. A second filtration through silica (8/2 AcOEt/heptane) makes it possible to obtain 3.88 g of Compound 3 in the form of an orange-yellow oil.

Yield: 29%.

$^1$H NMR (CDCl$_3$): 1.47 (s, 9H); 2.60 (m, 2H); 3.38 (m, 2H); 4.82 (broad s, 1H); 6.18 (dd, 1H); 6.88 (td, 1H); 9.55 (d, 1H).

A-4—Synthesis of N-BOC-5-amino-2-penten-1-al dimethylhydrazone (Compound 4)

3.88 g (19.5 mmol) of Compound 3 are added at 0° C. to 1.47 ml (19.5 mmol) of dimethylhydrazine and 8 drops of acetic acid in 30 ml of ether. The reaction mixture is left stirring for 10 min and the organic phase is separated by settling and washed with 1N HCl and then with a saturated NaCl solution. After drying over MgSO$_4$ and evaporating the solvent on a rotary evaporator, 4.4 g of hydrazone (Compound 4) are obtained in the form of an orange-yellow oil.

Yield: 94%.

$^1$H NMR (CDCl$_3$): 2.30 (s, 9H); 2.3 (m, 2H); 2.82 (m, 2H); 4.52 (broad s, 1H); 5.70 (td, 1H, J=6.8 and 15.6 Hz); 6.22 (ddd, 1H, J=0.8 and 8.8 and 15.6 Hz); 6.96 (d, 1H, J=8.8 Hz).

$^{13}$C NMR (CDCl$_3$): 28.15; 33.05; 39.58; 42.51; 78.77; 130.84; 130.95; 135;54; 155.68.

B—Preparation of the Compounds of Formula II and Ia

B-1: Synthesis of 4-methylpyrido[2,3-g]quinoline-5,10-dione (Intermediate I-1b) and of 4-methylpyrido-[3,2-g]quinoline-5,10-dione (Intermediate II-1b)

A mixture of 0.5 g (3.14 mmol) of quinoline-5,8-dione, 0.35 g (3.14 mmol) of crotonaldehyde dimethylhydrazone and 0.45 ml (4.76 mmol) of acetic anhydride in 20 ml of CHCl$_3$ are treated in an ultrasonic bath for 1 hour. After evaporating the solvent on a rotary evaporator, the reaction mixture is filtered through silica (CHCl$_3$) to give 0.428 g of a mixture of the two isomers I-1a and II-1a in the form of a purple powder. This powder and 1.6 g (18.4 mmol) of MnO$_2$ are suspended in 20 ml of CHCl$_3$ and the mixture is brought to reflux for 2 hours. After filtering through celite, the filtrate is concentrated on a rotary evaporator and then purified by flash chromatography on a silica column (98/2 CH$_2$Cl$_2$/MeOH) to give:

Intermediate (I-1b): 4-methylpyrido[2,3-g]quinoline-5,10-dione 40 mg (Yield: 6%) in the form of a brown powder.

Melting point: 220° C.

$^1$H NMR (CDCl$_3$): 2.91 (s, 3H); 7.54 (d, 1H, J=4.8 Hz); 7.75 (dd, 1H, J=4 and 7.6 Hz); 8.67 (dd, 1H, J=2 and 7.6 Hz); 8.91 (d, 1H, J=4.8 Hz); 9.12 (dd, 1H, J=2 and 4 Hz).

$^{13}$C NMR (CDCl$_3$): 22.75; 127.93; 128.04; 129.32; 131.50; 135.50; 148.73; 149.26; 152.11; 153.68; 155.47; 181.46; 182.87.

IR (CHCl$_3$): 1689 cm$^{-1}$.

Intermediate (II-1b): 4-methylpyrido[3,2-g]quinoline-5,10-dione 160 mg (Yield: 23%) in the form of a brown powder.

Melting point: 270° C.

$^1$H NMR (CDCl$_3$): 2.94 (s, 3H); 7.52 (d, 1H, J=4.8 Hz); 7.76 (dd, 1H, J=4.8 and 8.4 Hz); 8.59 (dd, 1H, J=2 and 8.4 Hz); 8.92 (d, 1H, J=–4.8 Hz); 9.11 (dd, 1H, J=2 and 4.8 Hz).

$^{13}$C NMR (CDCl$_3$): 22.81; 128.30; 128.39; 130.84; 131.55; 135.52; 147.90; 149.95; 151.74; 153.94; 155.35; 180.42; 184.02.

IR (CHCl$_3$) 1672; 1700.

B-2: Synthesis of 9-methoxy-4-methylpyrido[2,3-g] quinoline-5,10-dione (Intermediate I-2b) and of 6-methoxy-4-methylpyrido[3,2-g]quinoline-5,10-dione (Intermediate II-2b)

A mixture of 0.5 g (2.8 mmol) of 4-methoxyquinoline-5,8-dione, 0.32 g (2.87 mmol) of crotonaldehyde dimethylhydrazone and 0.4 ml (4.23 mmol) of acetic anhydride in 8 ml of CHCl$_3$ are brought to reflux for 1 hour. After evaporating the solvent on a rotary evaporator, the reaction mixture is filtered through silica (98/2 CH$_2$Cl$_2$/MeOH) to give 0.48 g of a mixture of the two isomers I-2a and II-2a in the form of a purple powder. This powder and 2.3 g (26.45 mmol) of MnO$_2$ are suspended in 26 ml of CHCl$_3$ and the mixture is brought to reflux for 2 hours. After filtering through celite, the filtrate is concentrated on a rotary evaporator and then purified by flash chromatography on a silica column (98/2 CH$_2$Cl$_2$/MeOH) to give:

Intermediate I-2b: 9-methoxy-4-methylpyrido[2,3-g]quinoline-5,10-dione 57 mg (Yield: 8%) in the form of a red powder.

$^1$H NMR (CDCl$_3$): 2.84 (s, 3H); 4.06 (s, 3H); 7.18 (d, 1H, J=6 Hz); 7.46 (d, 1H, J=4.4 Hz); 8.87 (d, 1H, J=6 Hz); 8.87 (d, 1H, J=4.4 Hz).

Intermediate II-2b: 6-methoxy-4-methylpyrido[3,2-g]quinoline-5,10-dione 293 mg (Yield: 40%) in the form of an orange powder.

$^1$H NMR (CDCl$_3$): 2.80 (s, 3H); 4.05 (s, 3H); 7.2 (d, 1H, J=6 Hz); 7.48 (d, 1H, J=4.8 Hz); 8.85 (d, 1H, J=6 Hz); 8.88 (d, 1H, J=4.8 Hz).

$^{13}$C NMR (CDCl$_3$): 21.75; 43.41; 112.74; 119.72; 130.93; 131.04; 148.32; 149.22; 150.26; 151.60; 152.80; 155.11; 181.44; 184.53.

IR (CHCl$_3$): 1675; 1700 cm$^{-1}$.

B-3: Synthesis of 9-nitro-4-methylpyrido[2,3-g]quinoline-5,10-dione (Intermediate I-5b) and of 6-nitro-4-methylpyrido[3,2-g]quinoline-5,10-dione (Intermediate II-5b)

A mixture of 0.8 g (3.92 mmol) of 4-nitroquinoline-5,8-dione, 0.65 g (5.8 mmol) of crotonaldehyde dimethylhydrazone and 0.55 ml (5.8 mmol) of acetic anhydride in 10.5 ml of CHCl$_3$ are treated in an ultrasonic bath for 30 min. After evaporating the solvent on a rotary evaporator, the reaction mixture is filtered through silica (98/2 CH$_2$Cl$_2$/MeOH) to give 0.7 g of a mixture of the two isomers I-5a and II-5a in the form of a purple powder. This powder and 2.9 g (33.4 mmol) of MnO$_2$ are suspended in 29 ml of CHCl$_3$ and the mixture is brought to reflux for 2 hours. After filtering through celite, the filtrate is concentrated on a rotary evaporator and then purified by flash chromatography on a silica column (98/2 CH$_2$Cl$_2$/MeOH) to give:

Intermediate I-5b: 9-nitro-4-methylpyrido[2,3-g]quinoline-5,10-dione 110 mg (Yield: 11%) in the powder form.

$^1$H NMR (CDCl$_3$): 2.98 (s, 3H); 7.19 (d, 1H, J=5.6 Hz); 7.54 (d, 1H, J=4.8 Hz); 8.79 (d, 1H, J=5.6 Hz); 8.94 (d, 1H, J=4.8 Hz).

IR (CHCl$_3$): 1703 cm$^{-1}$.

Intermediate II-5b: 6-nitro-4-methylpyrido[3,2-g]quinoline-5,10-dione 165 mg (Yield: 16%) in the form of a yellow-brown powder.

$^1$H NMR (CDCl$_3$): 2.85 (s, 3H); 7.6 (d, 1H, J=4.8 Hz); 7.74 (d, 1H, J=4.8 Hz); 8.99 (d, 1H, J=4.8 Hz); 9.33 (d, 1H, J=4.8 Hz).

B-4: Synthesis of 9-dimethylamino-4-methylpyrido[2,3-g]quinoline-5,10-dione (Intermediate I-3b) and of 6-dimethylamino-4-methylpyrido[3,2-g]quinoline-5,10-dione (Intermediate II-3b)

150 mg (0.558 mmol) of nitrated tricycle I-5a or II-5a and 0.4 ml (1.95 mmol) of N,N-dimethylformamide diethyl acetal are dissolved in 2.1 ml of DMF and the reaction mixture is heated at 130° C. for 1 hour. After evaporating the solvent with a vacuum pump, 140 mg of intermediate compound II-3a or II-3b are obtained, which material will be used as is in the following stage:

Intermediate II-3b: 6-dimethylamino-4-methylpyrido[3,2-g]quinoline-5,10-dione

Yield: 94%.

$^1$H NMR (CDCl$_3$): 2.77 (s, 3H); 3.05 (s, 6H); 6.89 (d, 1H, J=6 Hz); 7.39 (d, 1H, J=4.8 Hz); 8.42 (d, 1H, J=6 Hz); 8.74 (d, 1H, J=4.8 Hz).

B-5: Synthesis of 9-chloro-4-(N-BOC-1-aminoethane)-5,10-dihydropyrido[2,3-g]quinoline-5,10-dione (Intermediate I-7b) and of 6-chloro-4-(N-BOC-1-aminoethane)-5,10-dihydropyrido[3,2-g]quinoline-5,10-dione (Intermediate II-7b)

A mixture of 0.6 g (3.1 mmol) of 4-chloroquinoline-5,8-dione, 0.75 g (3.1 mmol) of dimethylhydrazone 4 and 0.45 ml (4.76 mmol) of acetic anhydride in 8.5 ml of CHCl$_3$ are treated in an ultrasonic bath for 30 min. After evaporating the solvent on a rotary evaporator, 2.7 g (31.1 mmol) of MnO$_2$ and 22 ml of CHCl$_3$ are added to the reaction mixture, which is brought to reflux for 2 hours. After filtering through celite, the filtrate is concentrated on a rotary evaporator and then purified by flash chromatography on a silica column (99/1 CH$_2$Cl$_2$/MeOH) to give:

Intermediate I-7b: 9-chloro-4-(N-BOC-1-aminoethane)-5,10-dihydropyrido[2,3-g]quinoline-5,10-dione:

70 mg (Yield: 6%) in the form of a brown powder.

$^1$H NMR (CDCl$_3$): 1.35 (s, 9H); 3.45–3.52 (m, 4H); 4.86 (broad s, 1H); 7.56 (d, 1H, J=4.0 Hz); 7.74 (d, 1H, J=5.2 Hz); 8.90 (d, 1H, J=5.2 Hz); 8.94 (d, 1H, J=4 Hz).

$^{13}$C NMR (CDCl$_3$): 28.37; 35.32; 40.30; 79.47; 126.84; 128.04; 130.88; 131.17; 145.78; 150.34; 150.98; 152.29; 154.05; 154.36; 155.88; 179.76; 182.32.

IR (CHCl$_3$): 1695 cm$^{-1}$.

Intermediate II-7b: 6-chloro-4-(N-BOC-1-aminoethane)-5,10-dihydropyrido[3,2-g]quinoline-5,10-dione 200 mg (Yield: 17%) in the form of a brown powder.

$^{13}$C NMR (CDCl$_3$): 28.24; 34.96; 40.33; 79.47; 128.46; 130.15; 131.06; 131.59; 145.20; 148.76; 149.71; 151.74; 153.88; 153.92; 155.84; 179.76; 183.20.

IR (CHCl$_3$): 1705 cm$^{-1}$.

B-6: Synthesis of 3-methoxy-4-methylpyrido[2,3-g]quinoline-5,10-dione (Intermediate I-8b) and of 3-methoxy-4-methylpyrido[3,2-g]quinoline-5,10-dione (Intermediate II-8b)

A mixture of 1 g (6.28 mmol) of quinoline-5,8-dione and 1.78 g (12.57 mmol) of 2-methoxy-2-butenal dimethylhydrazone in 25 ml of CHCl$_3$ are stirred at ambient temperature for 5 hours. After evaporating the solvent on a rotary evaporator, the reaction mixture is filtered through silica (95/5 CH$_2$Cl$_2$/MeOH) to give 1.55 g of a mixture of the two isomers I-8a and II-8a in the form of a purple powder. This powder and 1 g (11.5 mmol) of MnO$_2$ are suspended in 30 ml of CHCl$_3$ and the mixture is stirred at ambient temperature for 1 hour. After filtering through celite, the filtrate is concentrated on a rotary evaporator and then purified by flash chromatography on a silica column (99/1 CH$_2$Cl$_2$/MeOH) to give:

Intermediate I-8b: 3-methoxy-4-methylpyrido[2,3-g]quinoline-5,10-dione 110 mg (Yield: 7%) in the form of a brown powder.
Melting point: >260° C.
$^1$H NMR (CDCl$_3$): 2.79 (s, 3H); 4.11 (s, 3H); 7.72 (dd, 1H, J=4.8 and 8,1 Hz); 8.66 (s, 1H); 8.67 (dd, 1H, J=8.1 and 1.9 Hz); 9.10 (dd, 1H, J=4.8 and 1.9 Hz).
$^{13}$C NMR (CDCl$_3$): 13.03; 56.87; 127.88; 129.50; 129.95; 135.50; 136.64; 139.26; 142.56; 149.33; 155.11; 157.24; 180.63; 183.56.
IR (CHCl$_3$): 1684 cm$^{-1}$.

Intermediate II-8b: 3-methoxy-4-methylpyrido[3,2-g]quinoline-5,10-dione 190 mg (Yield: 12%) in the form of a brown powder.
Melting point: >260° C.
$^1$H NMR (CDCl$_3$): 2.77 (s, 3H); 4.12 (s, 3H); 7.74 (dd, 1H, J=4.6 and 8.0 Hz); 8.60 (dd, 1H, J=8.0 and 1.6 Hz); 8.68 (s, 1H); 9.12 (dd, 1H, J=4.6 and 1.6 Hz).
$^{13}$C NMR (CDCl$_3$): 12.98; 56.93; 127.99; 129.06; 131.27; 135.53; 136.84; 138.81; 143.27; 148.16; 155.20; 157.16; 179.69; 184.59.
IR (CHCl$_3$): 1670; 1692 cm$^{-1}$.

B-7: Synthesis of 3,9-dimethoxy-4-methylpyrido[2,3-g]quinoline-5,10-dione (Intermediate I-9b) and of 3,6-dimethoxy-4-methylpyrido[3,2-g]quinoline-5,10-dione (Intermediate II-9b)

A solution of 2-methoxy-2-butenal dimethylhydrazone (1 g, 7.1 mmol) in 15 ml of chloroform is added dropwise to a solution of 4-methoxyquinolinedione (1.33 g, 7 mmol) in 30 ml of chloroform. The reaction mixture is kept stirred at ambient temperature, under nitrogen and with the exclusion of light for 5 hours. After evaporating the solvent on a rotary evaporator, the crude product obtained is purified by flash chromatography through silica (CHCl$_3$, then 98/2 CHCl$_3$/MeOH, then 95/5 CHCl$_3$/MeOH) to produce a first fraction F$_1$ comprising the nonaromatic product and a second fraction F$_2$ comprising the expected product. 1 g of MnO$_2$ is added to the fraction F1 and 30 ml of chloroform. The mixture is left stirring for 90 min. After filtering through celite and washing the precipitate with CHCl$_3$ and then with MeOH, the filtrate is concentrated on a rotary evaporator to produce a fraction F$_{1'}$. The fractions F$_{1'}$ and F$_2$ are combined and then purified by flash chromatography through silica (CHCl$_3$ and then 97/3 CHCl$_3$/MeOH) to give the two expected compounds I-9a and II-9b in the form of a brown powder.

Intermediate (II-9b): 3,6-dimethoxy-4-methylpyrido[3,2-g]quinoline-5,10-dione

Yield: 11% (210 mg).
Melting point: >260° C.
$^1$H NMR (CDCl$_3$): 2.68 (s, 3H) 4.09 (s, 3H); 4.10 (s, 3H); 7.18 (d, 1H, J=5.5 Hz); 8.60 (s, 1H); 8.88 (d, 1H, J=5.5 Hz).
$^{13}$C NMR (CDCl$_3$): 12.85; 56.81; 56.84; 111.14; 121.32; 130.95; 136,43; 137.79; 141.95; 150.31; 155.44; 157.33; 165.97; 180.13; 184.24.
IR (CHCl$_3$): 1678, 1692 cm$^{-1}$.

B-8—Synthesis of 3-methoxy-4-methyl-9-chloropyrido[2,3-g]quinoline-5,10-dione (Intermediate I-10b) and of 3-methoxy-4-methyl-6-chloropyrido[3,2-g]quinoline-5,10-dione (Intermediate II-10b)

A solution of 2-methoxy-2-butenal dimethylhydrazone (1 g, 7.1 mmol) in 15 ml of chloroform is added dropwise to a solution of 4-chloroquinolinedione (1.37 g, 7.1 mmol) in 30 ml of chloroform. The reaction mixture is kept stirred at ambient temperature, under nitrogen and with the exclusion of light, for 5 h 30. After evaporating the solvent on a rotary evaporator, the crude product obtained is purified by flash chromatography through silica (CHCl$_3$, then 98/2 CHCl$_3$/MeOH) to produce a first fraction F$_1$ comprising the non-aromatic product. 1 g of MnO$_2$ is added to this fraction F$_1$ and 30 ml of chloroform. The mixture is left stirring at ambient temperature for 60 min. After filtering through celite and washing the precipitate with CHCl$_3$ and then with MeOH, the mixture is concentrated on a rotary evaporator. The crude product obtained is purified by flash chromatography through silica (97/3 [lacuna]) to give the compounds I-10b and II-10b in the form of a yellow powder.

Intermediate II-10b: 3-methoxy-4-methyl-6-chloropyrido[3,2-g]quinoline-5,10-dione Yield: 5% (100 mg).
Melting point: >260° C.
$^1$H NMR (CDCl$_3$): 2.68 (s, 3H); 4.11 (s, 3H); 7.71 (d, 1H, J=5.2 Hz); 8.64 (s, 1H); 8.90 (d, 1H, J=5.2 Hz).
$^{13}$C NMR (CDCl$_3$): 12.96; 56.97; 128.92; 130.72; 130.98; 136.95; 138.12; 141.93; 145.06; 150.21; 153.85; 157.55; 179.31; 183.67.
IR (CHCl$_3$): 1696; 1684 cm$^{-1}$.

B-9: Synthesis of 3-methoxy-4-methyl-9-dimethylaminopyrido[2,3-g]quinoline-5,10-dione (Intermediate I-11b) and of 3-methoxy-4-methyl-6-dimethylaminopyrido[3,2-g]quinoline-5,1-dione (Intermediate II-11b)

A solution of I-10b or of II-10b (90 mg, 0.31 mmol), of dimethylammonium chloride (127 mg, 1.56 mmol) and of NaOH (63 mg, 1.56 mmol) in a THF/H$_2$O (4 ml/2 ml) mixture is brought to reflux for 1 hour. After evaporating the solvent on a rotary evaporator, the crude product obtained is taken up in a 95/5 CH$_2$Cl$_2$/MeOH mixture (50 ml). The organic phase is recovered and then dried over MgSO$_4$. After concentrating on a rotary evaporator, the crude product obtained is purified by flash chromatography through silica (95/5 CH$_2$Cl$_2$/MeOH) to give the expected compounds I-11b or II-11b in the form of a yellow powder.

Intermediate II-11b: 3-methoxy-4-methyl-6-dimethylaminopyrido[3,2-glquinoline-5,10-dione Yield: 87% (80 mg).
Melting point: >260° C.
$^1$H NMR (CDCl$_3$): 2.64 (s, 3H); 3.06 (s, 6H); 4.08 (s, 3H); 6.95 (d, 1H, J=5.9 Hz); 8.53 (d, 1H, J=5.9 Hz); 8.56 (s, 1H).
$^{13}$C NMR (CDCl$_3$): 12.62; 43.40; 56.80; 112.39; 120.50; 132.23; 135.90; 136.08; 141.86; 150.53; 151.70; 155.04; 157.19; 180.67; 185.45.
IR (CHCl$_3$): 1693; 1654 cm$^{-1}$.

B-10: Synthesis of 3,7-dimethoxy-4-methylpyrido[2,3-g]quinoline-5,10-dione (Intermediate I-12b) and of 3,8-dimethoxy-4-methylpyrido[3,2-g]quinoline-5,10-dione (Intermediate II-12b)

1—Synthesis of 2-methoxyquinoline-5,8-dione

A suspension of 5,8-dioxocarbostyryl (3.1 g, 17.7 mmol), of silver carbonate (10.2 g, 37 mmol) and of methyl iodide (31 ml, 498 mmol) in 1.2 l of CHCl$_3$ is stirred in the dark at ambient temperature for 90 hours. The precipitate is removed by filtration and the filtrate is concentrated on a rotary evaporator. The crude product obtained is purified by filtration through silica (CHCl$_3$) to give the expected quinone in the form of a yellow solid (2.2 g).

Yield: 66%).
Melting point: 196° C.
$^1$H NMR (CDCl$_3$): 4.14 (s, 3H); 6.95 (d, 1H, J=10.3 Hz); 7.02 (d, 1H, J=10.3 Hz); 7.06 (d, 1H, J=8.8 Hz); 8.25 (d, 1H, J=8.8 Hz).
$^{13}$C NMR (CDCl$_3$): 54.70; 116.68; 124.32; 136.83; 137.54; 138.21; 146.58; 167.14; 183.48; 184.31.

2—Synthesis of 3,7-dimethoxy-4-methylpyrido[2,3-g]quinoline-5,10-dione (Intermediate I-12b) and of 3,8- dimethoxy-4-methylpyrido[3,2-g]quinoline-5,10-dione (Intermediate II-12b)

A solution of 2-methoxy-2-butanal dimethylhydrazone (0.75 g, 5.3 mmol) in 10 ml of THF is added dropwise to a solution of methoxyquinolinedione (1.0 g, 5.3 mmol) in 60 ml of THF. The reaction mixture is kept stirred at ambient temperature, under nitrogen and with the exclusion of light, for 40 hours. After evaporating the solvent on a rotary evaporator, the crude product obtained is dissolved in 80 ml of $CHCl_3$ and 85% $MnO_2$ (5.4 g, 53 mmol) is added. The reaction mixture is kept stirred for 2 hours and is then filtered through celite. After concentrating on a rotary evaporator, the crude product obtained is purified by flash chromatography through silica ($CHCl_3$) to give the compounds I-12b and II-12b in the form of a brown powder.

Intermediate II-12b: 3,8-dimethoxy-4-methylpyrido[3,2-g]quinoline-5,10-dione

Yield: 8% (120 mg).
Melting point: >260° C.
$^1$H NMR ($CDCl_3$): 2.74 (s, 3H); 4.09 (s, 3H); 4.20 (s, 3H); 7.09 (d, 1H, J=8.4 Hz); 8.41 (d, 1H, J=8.4 Hz); 8.63 (s, 1H).
$^{13}$C NMR ($CDCl_3$):
IR ($CHCl_3$): 1667, 1693 $cm^{-1}$.

B-11: Synthesis of 8-ethoxycarbonyl-8-(2'-N-BOC-aminoethyl)pyrido[2,3-g]quinoline-5,10-dione (Intermediate I-13b) and of 7-ethylcarbonyl-6(2'-N-BOC-aminoethyl)pyrido[3,2-g]quinoline 5,10-dione (Intermediate II-13b)

A solution of N-BOC-5-amino-2-penten-1-al dimethylhydrazone (1.1 g, 4.56 mmol) in 15 ml of acetonitrile is added dropwise to a solution of 3-ethylquinolinecarboxylate-5,8-dione (1.05 g, 4.54 mmol) and of acetic anhydride (4.6 ml) in 75 ml of acetonitrile. The reaction mixture is kept stirred at ambient temperature, under nitrogen and with the exclusion of light, for 24 hours. After evaporating the solvent on a rotary evaporator, 5 g of $MnO_2$ and 150 ml of chloroform are added to the crude product obtained. The mixture is left stirring at ambient temperature for 1 h 30. After filtering through celite and washing the precipitate with $CHCl_3$ and then with MeOH, the mixture is concentrated on a rotary evaporator. The crude product obtained is purified, first by filtration through silica (99/1 and then 97/3 $CH_2Cl_2$/MeOH) and then by flash chromatography through silica (99/1), to give the compounds I-13b and II-13b in the form of a brown powder.

Intermediate II-13b: 7-ethoxycarbonyl-6-(2'-N-BOC-aminoethyl)pyrido[3,2-g]quinoline-5,10-dione Yield: 3% (60 mg).
Melting point: 170° C.
$^1$H NMR ($CDCl_3$): 1.36 (s, 9H); 1.47 (t, 3H, J=7.4 Hz); 3.52 (m, 4H); 4.51 (q, 2H, J=7.4 Hz); 4.78 (broad 9, 1H); 7.57 (d, 1H, J=5.2 Hz); 8.99 (d, 1H, J=5.2 Hz); 9.17 (d, 1H, J=2.2 Hz); 9.64 (d, 1H, J=2.2 Hz).
$^{13}$C NMR ($CDCl_3$): 14.33; 28.40; 35.74; 40.22; 62.62; 79.63; 128.65; 130.33; 130.49; 131.83; 137.30; 149.60; 150.23; 152.72; 154.23; 155.72; 155.98; 163.52; 179.69; 183.38.
IR ($CHCl_3$): 3457; 1726; 1705; 1677 $cm^{-1}$.

B-12: Synthesis of 7-hydroxy-4-(2'-N-Boc-aminoethyl)pyrido[2,3-g]quinoline-5,10-dione (Intermediate I-14b) and of 8-hydroxy-4-(2'-N-Boc-aminoethyl)pyrido[3,2-g]quinoline-5,10-dione (Intermediate II-14b)

A solution of N-BOC-5-amino-2-penten-1-al dimethylhydrazone (1.49 g, 6.15 mmol) in 30 ml of acetonitrile is added dropwise to a solution of 5,8-dioxocarbostyril (0.98 g, 5.59 mmol) and of acetic anhydride (5.8 ml) in 100 ml of acetonitrile. The reaction mixture is kept stirred at ambient temperature, under nitrogen and with the exclusion of light, for 16 hours. After evaporating the solvent on a rotary evaporator, 7 g (80.5 mmol) of $MnO_2$ and 180 ml of chloroform are added to the crude product obtained. The mixture is left stirring at ambient temperature for 1 h 30. After filtering through celite and washing the precipitate with $CHCl_3$ and with MeOH, the mixture is concentrated on a rotary evaporator. The crude product obtained is purified by filtration through silica (98/2 and then 95/5 $CH_2Cl_2$/MeOH) to give the compound I-14b and II-14b in the form of a brown powder.

Intermediate II-14b: 8-hydroxy-4-(2'-N-Boc-aminoethyl)pyrido[3,2-g]quinoline-5,10-dione Yield: 12% (230 mg).
Melting point: 252° C.
$^1$H NMR ($CDCl_3$): 1.56 (s, 9H); 3.49 (m, 4H); 4.73 (broad s, 1H); 6.94 (d, 1H, J=9.6 Hz); 7.54 (d, 1H, J=4.8 Hz); 8.10 (d, 1H, J=9.6 Hz); 8.89 (d, 1H, J=4.8 Hz); 9.66 (broad s, 1H).
$^{13}$C NMR ($CDCl_3$): 28.29; 35.53; 40.24; 117.01; 127.87; 128.62; 132.29; 136.18; 138.04; 148.25; 152.26; 153.33; 155.86; 176.36; 181.35.
IR ($CHCl_3$): 3457; 3340; 1693; 1663 $cm^{-1}$.

B-13: Synthesis of 7-hydroxy-4-methylpyrido[2,3-g]quinoline-5,10-dione (Intermediate I-15b) and of 8-hydroxy-4-methylpyrido[3,2-g]quinoline-5,10-dione (Intermediate II-15b)

A solution of 2-butenal dimethylhydrazone (0.703 g, 6.28 mmol) in 20 ml of acetonitrile is added dropwise to a solution of 5,8-dioxocarbostyril (1 g, 5.71 mmol) and of acetic anhydride (6.2 ml) in 220 ml of acetonitrile. The reaction mixture is kept stirred at ambient temperature, under nitrogen and with the exclusion of light, for 16 hours and is then heated at reflux for 6 hours. After evaporating the solvent on a rotary evaporator, the crude product obtained is purified by filtration through silica ($CH_2Cl_2$ and then 98/2 $CH_2Cl_2$/MeOH) to produce a first fraction comprising the nonaromatic product and the expected product. 3 g of $MnO_2$ and 75 ml of chloroform are added to the mixture, which is left stirring at ambient temperature overnight. After filtering through celite and washing the precipitate with $CHCl_3$ and then with MeOH, the mixture is concentrated on a rotary evaporator. The crude product obtained is purified by flash chromatography through silica (99/1) to give the expected compounds I-15b and II-15b in the form of a beige powder.

Intermediate II-15b: 8-hydroxy-4-methylpyrido[3,2-g]quinoline-5,10-dione

Yield: 12%.
Melting point: >260° C.
$^1$H NMR ($d_6$-DMSO): 2.79 (s, 3H); 6.82 (d, 1H, J=9.5 Hz); 7.73 (d, 1H, J=5.2 Hz); 8.05 (d, 1H, J=9.5 Hz); 8.85 (d, 1H, J=5.2 Hz); 12.27 (broad s, 1H).
$^{13}$C NMR ($d_6$-DMSO): 21.92; 114.30; 122.66; 127.30; 131.52; 135.94; 148.60; 149.80; 152.48 (2C); 176.41; 182.13 (2C).
IR ($CHCl_3$): 1684; 1664 $cm^{-1}$.

B-14: Synthesis of 7-methoxy-4-methylpyrido[2,3-g]quinoline-5,10-dione (Intermediate I-16b) and of 8-methoxy-4-methylpyrido[3,2-g]quinoline-5,10-dione (Intermediate II-16b)

A mixture of compound I-15b or II-15b (70 mg, 0.29 mmol), of methyl iodide (1 ml, 15.9 mmol) and of $Ag_2CO_2$ (170 mg, 0.62 mmol) in 100 ml of $CHCl_3$ is stirred at ambient temperature and with the exclusion of light for 14 hours and is then heated at 56° C. for 5 hours. After concentrating on a rotary evaporator, the crude product obtained is purified by flash chromatography through silica (99.5/0.5 $CH_2Cl_2$/MeOH) to give the expected compounds I-16b or II-16b in the form of a beige-brown powder.

Intermediate II-16b: 8-methoxy-4-methylpyrido[3,2-g]quinoline-5,10-dione.
Yield: 41% (30 mg).
Melting point: 128° C.
$^1$H NMR (CDCl$_3$): −4.14 (s, 3H); 7.07 (d, 1H, J=8.8 Hz); 7.44 (d, 1H, J=4.8 Hz); 8.37 (d, 1H, J=8.8 Hz); 8.85 (d, 1H, J=4.8 Hz).
$^{13}$C NMR (CDCl$_3$): 54.92; 117.58; 126.24; 128.09; 131.30; 137.73; 147.31; 150.00; 151.34; 153.38; 167.39; 180.44; 183.70.
IR (CHCl$_3$): 1765; 1698; 1667; 1603 cm$^{-1}$.

B-15: Synthesis of 7,9-dichloro-4-methylpyrido[2,3-g]quinoline-5,10-dione (Intermediate I-17b) and of 6,8-dichloro-4-methylpyrido[3,2-g]quinoline-5,10-dione (Intermediate II-17b)

1. Synthesis of 2,4-dichloroquinoline-5,8-dione

Cerium ammonium nitrate (CAN 21.4 g, 39.03 mmol) is added portionwise to a solution of 2,4-dichloro-5,8-dimethoxyquinoline (2.85 g, 11.04 mmol) in a CH$_3$CN/H$_2$O mixture (150 ml/75 ml). The reaction mixture is stirred at ambient temperature for 40 min. The acetonitrile is subsequently evaporated and 50 ml of water and 200 ml of a saturated NaHCO$_3$ solution are added. The aqueous phase is extracted with CH$_2$Cl$_2$ (5 times 200 ml). After drying over MgSO$_4$, the solvent is evaporated on a rotary evaporator to give the expected compound in the form of a brown powder (1.9 g).
Yield: 75%.
Melting point: 161° C.
$^1$H NMR (CDCl$_3$): 7.03 (d, 1H, J=10.6 Hz); 7.11 (d, 1H, J=10.6 Hz); 7.74 (s, 1H).
$^{13}$C NMR (CDCl$_3$): 124.43; 131.10; 136.91; 139.52; 146.69; 148.96; 156.16; 180.53; 182.01.
IR (CHCl$_3$): 1687; 1676 cm$^{-1}$.

2. Synthesis of 7,9-dichloro-4-methylpyrido[2,3-g]quinoline-5,10-dione (Intermediate I-17b) and of 6,8-dichloro-4-methylpyrido[3,2-g]quinoline-5,10-dione (Intermediate II-17b)

A solution of 2-butenal dimethylhydazone (0.325 g, 2.89 mmol) in 20 ml of acetonitrile is added dropwise to a solution of 2,4-dichloroquinoline-5,8-dione (0.6 g, 2.63 mmol) and of acetic anhydride (5 ml) in 100 ml of acetonitrile. The reaction mixture is kept stirred at ambient temperature, under nitrogen and with the exclusion of light, for 20 hours. After evaporating the solvent on a rotary evaporator, the crude product obtained is taken up in 140 ml of CHCl$_3$. 3.65 g of MnO$_2$ are subsequently added and then the mixture is left stirring at ambient temperature for 56 hours. After filtering through celite and washing the precipitate with CHCl$_3$ and then with MeOH, the solution is concentrated on a rotary evaporator. The crude product obtained is purified by flash chromatography through silica (CH$_2$Cl$_2$) to give the expected compounds I-17b and II-17b in the form of a brown powder.
Intermediate II-17b: 6,8-dichloro-4-methylpyrido[3,2-g]quinoline-5,10-dione
Yield: 41% (314 mg).
Melting point: 177° C.
$^1$H NMR (CDCl$_3$): 2.87 (s, 3); 7.56 (d, 1H, J=4.8 Hz); 7.79 (s, 1H); 8.93 (d, 1H, J=4.8 Hz).
$^{13}$C NMR (CDCl$_3$): 22.41; 125.44; 127.84; 131.13; 131.30; 147.44; 149.81; 150.62; 151.90; 154.30; 156.58; 179.12; 180.66.
IR (CHCl$_3$): 1706; 1683 cm$^{-1}$.

B-16—Synthesis of 7,9-dimethoxy-4-methylpyrido[2,3-g]quinoline-5,10-dione (Intermediate 1-18b) and of 6,8-dimethoxy-4-methylpyrido[3,2-g]quinoline-5,10-dione (Intermediate II-18b)

A mixture of compound I-17b or of compound II-17b (80 mg, 0.27 mmol) and of sodium methoxide (300 mg of Na in 40 ml of methanol, 13.04 mmol) in 40 ml of methanol is brought to reflux for 17 hours. The reaction mixture is concentrated to dryness and then 50 ml of water are added. After neutralizing with 25% HCl, the solution is extracted with CH$_2$Cl$_2$ (3 times 50 ml). After drying over MgSO$_4$ and evaporating the solvent on a rotary evaporator, the expected compounds I-18b or II-18b [lacuna] quantitatively.
Intermediate II-18b: 6,8-dimethoxy-4-methylpyrido[3,2-g]quinoline-5,10-dione
Melting point: 219° C.
$^1$H NNR (CDCl$_3$): 2.88 (s, 1H); 4.03 (s, 3H); 4.07 (s, 3H); 6.53 (s, 1H); 7.45 (d, 1H, J=4.8 Hz); 8.83 (d, 1H, J=4.8 Hz).
$^{13}$C NMR (CDCl$_3$): 22.64; 54.73; 56.80; 97.79; 117.61; 129.55; 131.46; 148.67; 149.41; 150.73; 152.96; 167.95; 168.00; 180.91; 183.41.
IR (CHCl$_3$): 1701; 1668 cm$^{-1}$.

EXAMPLE 1

7H-Pyrido[4,3,2-de][1,10]phenanthroline-7-one (CRL 8293) and 7-pyrido[4,3,2-de][1,7]phenanthroline-7-one (CRL 8294)

63 mg (2.81 mmol) of compound I-b and 1.7 ml (9.84 mmol) of dimethylformamide diethyl acetal in 4.5 ml of DMF are brought to 120° C., under nitrogen, for 1 hour. After evaporating the solvent with a vacuum pump, 3.5 g (65 mmol) of NH$_4$Cl and 60 ml of absolute ethanol are added. The reaction mixture is brought to reflux for 30 min. After evaporating the ethanol on a rotary evaporator, 50 ml of water are added to the residue and extraction is carried out with CH$_2$Cl$_2$ (3 times 50 ml). After drying the organic phases over MgSO$_4$ and evaporating the solvent on a rotary evaporator, 0.6 g of CRL 8294 are obtained in the form of a greenish powder.

7H-Pyrido[4,3,2-de][1,10]phenanthroline-7-one (CRL 8293)

Yield: 90%.
Melting point: 240° C.
$^1$H NMR (CDCl$_3$): 7.68 (dd, 1H, J=4.4 and 8 Hz); 7.87 (d, 1H, J=5.6 Hz); 8.02 (d, 1H, J=5.2 Hz); 8.77 (dd, 1H, J=1.6 and 8 Hz); 9.11 (d, 1H, J=5.2 Hz); 9.16 (dd, 1H, J=1.6 and 4.4 Hz); 9.19 (d, 1H, J=5.6 Hz).
$^{13}$C NMR (CDCl$_3$): 120.95; 124.40; 126.14; 129.32; 136.78; 139.09; 147.45; 148.58; 148.82; 148.96; 150.66; 152.00; 155.73; 181.96.

7H-Pyrido[4,3,2-de][1,7phenanthroline-7-one (CRL 8294)

By following the procedure described above starting from the intermediate II-1b, 72 mg of compound CRL 8294 are obtained in the form of a yellow powder.
Yield: 80%.
$^1$H NMR (CDCl$_3$): 7.76 (dd, 1H, J=4.4 and 8 Hz); 7.80 (d, 1H, J=5.2 Hz); 7.99 (d, 1H, J=5.6 Hz); 8.93 (d, 1H, J=5.6 Hz); 9.05 (dd, 1H, J=1.6 and 4.4 Hz); 9.17 (dd, 1H, J=1.6 and 8 Hz); 9.19 (d, 1H, J=5.2 Hz)
$^{13}$C NMR (CDCl$_3$): 119.39; 120.01; 123.85; 128.15; 132.87; 133.80; 138.65; 147.54; 147.74; 148.93; 149.49; 149.99; 152.97; 180.73.

EXAMPLE 2

8-Methoxy-7H-pyrido[4,3,2-de][1,10]phenanthroline-7-one (CRL 8363) and 11-methoxy-7H-pyrido[4,3,2-de][1,7]phenanthroline-7-one (CRL 8364)

74 mg (2.92 mmol) of compound I-2b and 2 ml (11.8 mmol) of dimethylformamide diethyl acetal in 5.2 ml of DMF are brought to 120° C., under nitrogen, for 1 hour. After evaporating the solvent with a vacuum pump, 4.5 g (83.6 mmol) of $NH_4Cl$ and 67 ml of absolute ethanol are added. The reaction mixture is brought to reflux for 30 min. After evaporating the ethanol on a rotary evaporator, 50 ml of water are added to the residue and extraction is carried out with $CH_2Cl_2$ (3 times 50 ml). After drying the organic phases over $MgSO_4$ and evaporating the solvent on a rotary evaporator, the residue is purified by flash chromatography on a silica column (98/2 $CHCl_3$/MeOH) to give 0.28 g of compound CRL 8363 in the form of an orange powder.

8-Methoxy-7H-pyrido[4,3,2-de][1,10] phenanthroline-7-one (CRL 8363)

Yield: 37%.

$^1$H NMR ($CDCl_3$): 4.20 (s, 3H); 7.13 (d, 1H, J=5.6 Hz); 7.82 (d, 1H, J=5.2 Hz); 7.94 (d, 1H, J=6 Hz); 8.92 (d, 1H, J=5.6 Hz); 9.07 (d, 1H, J=6 Hz); 9.13 (d, 1H, J=5.2 Hz); 9.19 (d, 1H, J=5.2 Hz).

$^{13}$C NMR ($CDCl_3$): 56.77; 109.26; 119.70; 120.47; 123.09; 138.50; 147.85; 148.25; 148.69; 150.66; 154.08; 155.68; 167.54; 180.40.

11-Methoxy-7H-pyrido[4,3,2-de][1,10] phenanthroline-7-one (CRL 8364)

By following the procedure described above starting from 1.14 g of the intermediate II-2b, 0.59 g of compound CRL 8364 are obtained in the form of a yellow powder.

Yield: 50%.

$^1$H NMR ($CDCl_3$): 4.15 (s, 3H); 7.26 (d, 1H, J=6 Hz); 7.70 (d, 1H, J=6 Hz); 7.96 (d, 1H, J=5.6 Hz); 8.85 (d, 1H, J=6 Hz); 8.97 (d, 1H, J=6 Hz); 9.15 (d, 1H, J=5.6 Hz).

$^{13}$C NMR ($CDCl_3$): 57.05; 111.33; 118.72; 119.61; 122.12; 124.29; 138.56; 146.71; 147.10; 148.69; 149.81; 150.96; 153.13; 165.83; 180.82.

EXAMPLE 3

8-(Dimethylamino)-7H-pyrido[4,3,2-de][1,10] phenanthroline-7-one (CRL 8800) and 11-(dimethylamino)-7H-pyrido[4,3,2-de][1,7] phenanthroline-7-one (CRL 8367)

80 mg (0.3 mmol) of tricycle I-3b or of tricycle II-3b and 0.21 ml (1.05 mmol) of dimethylformamide diethyl acetal in 1.2 ml of DMF are brought to 120° C., under nitrogen, for 1 hour. After evaporating the solvent with a vacuum pump, 0.5 g (9.3 mmol) of $NH_4Cl$ and 80 ml of absolute ethanol are added. The reaction mixture is brought to reflux for 40 min. After evaporating the ethanol on a rotary evaporator, 5 ml of water are added to the residue and extraction is carried out with $CH_2Cl_2$ (3 times 5 ml). After drying the organic phases over $MgSO_4$ and evaporating the solvent on a rotary evaporator, the two tetracyclic compounds are obtained quantitatively in the form of a red powder.

11-(Dimethylamino)-7H-pyrido[4,3,2-de][1,7] phenanthroline-7-one (CRL 8367)

$^1$H NMR ($CDCl_3$): 3.00 (s, 6H); 7.09 (d, 1H, J=5.2 Hz); 7.57 (d, 1H, J=5.6 Hz); 7.90 (d, 1H, J=5.2 Hz); 8.54 (d, 1H, J=5.2 Hz); 8.89 (d, 1H, J=5.2 Hz); 9.11 (d, 1H, J=5.6 Hz).

EXAMPLE 4

8-Hydroxy-7H-pyrido[4,3,2-de][1,10] phenanthroline-7-one (CRL 8802) and 11-hydroxy-7H-pyrido[4,3,2-de][1,7]phenanthroline-7-one (CRL 8388)

50 mg (0.126 mmol) of tricycle I-7b or of tricycle II-7b are dissolved in 0.5 ml of TFA and then the reaction mixture is stirred for 24 hours. The TFA is evaporated on a rotary evaporator and then a saturated $NaHCO_3$ solution is added until a pH of 9–10 is obtained. The mixture is extracted with $CH_2Cl_2$ (3 times 3 ml). After drying over $MgSO_4$ and evaporating the solvent on a rotary evaporator, 20 mg of tetracyclic compound are obtained in the form of a yellow powder.

11-Hydroxy-7H-pyrido[4,3,2-de][1,7] phenanthroline-7-one (CRL 8388)

Yield: 62%.

Melting point: >260° C.

$^1$H NMR ($CDCl_3$): 7.20 (d, 1H, J=5.6 Hz); 7.83 (d, 1H, J=6 Hz); 8.00 (d, 1H, J=6 Hz); 8.72 (d, 1H, J=6 Hz); 8.76 (d, 1H, J=6 Hz); 9.24 (d, be 1H, J=5.6 Hz), 14.65 (s, 1H).

$^{13}$C NMR ($d_6$-DMSO): 116.22; 116.35; 118.61; 120.24; 124.06; 138.09; 143.61; 148.04; 148.99; 149.41; 152.61; 153.01; 165.80; 179.55.

EXAMPLE 5

8-Chloro-7H-pyrido[4,3,2-de][1,10]phenanthroline-7-one (CRL 8396) and 11-chloro-7H-pyrido[4,3,2-de][1,7]phenanthroline-7-one (CRL 8801)

260 mg (0.67 mmol) of tricycle I-7b or of tricycle II-7b are dissolved in 2.6 ml of TFA and then the reaction mixture is stirred for 64 hours. The TFA is evaporated on a rotary evaporator and then 200 ml of 95/5 $CH_2Cl_2$/MeOH are added, followed by a saturated $NaHCO_3$ solution until a pH of 10 is obtained. The organic phase is recovered and is washed with water. After drying over $MgSO_4$ and evaporating the solvent on a rotary evaporator, 40 mg of tetracyclic compounds are obtained in the form of a brown powder which is washed with ether.

8-Chloro-7H-pyrido[4,3,2-de][1,7]phenanthroline-7-one (CRL 8396)

Yield: 28%.

Melting point: >260° C.

$^1$H NMR ($CDCl_3$): 7.68 (d, 1H, J=5.2 Hz); 7.89 (d, 1H, J=5.5 Hz); 8.01 (d, 1H, J=5.5 Hz); 8.96 (d, 1H, J=5.2 Hz); 9.14 (d, 1H, J=5.5 Hz); 9.19 (d, 1H, J=5.5 Hz).

$^{13}$C NMR ($d_6$-DMSO): 119.87; 120.88; 123.61; 126.31; 129.01; 138.56; 146.87; 147.37; 148.46; 148.94; 149.76; 153.85; 153.96; 179.87.

EXAMPLE 6

4-Methoxy-7H-pyrido[4,3,2-de][1,10] phenanthroline-7-one (CRL 8400) and 4-methoxy-7H-pyrido[4,3,2-de][1,7]phenanthroline-7-one (CRL 8401)

100 mg (0.39 mmol) of tricycle I-8b or of tricycle II-8b and 0.27 ml (1.37 mmol) of dimethylformamide diethyl acetal in 0.7 ml of DMF are brought to 120° C., under nitrogen, for 1 hour. After evaporating the solvent with a vacuum pump, 0.6 g (11.7 mmol) of $NH_4Cl$ and 90 ml of absolute ethanol are added. The reaction mixture is brought to reflux for 30 min. After evaporating the ethanol on a rotary evaporator, 10 ml of water are added to the residue and extraction is carried out with $CH_2Cl_2$ (3 times 10 ml). After drying the organic phases over $MgSO_4$, evaporating the solvent on a rotary evaporator and purifying by filtration through silica (95/5 $CH_2Cl_2$/MeOH), the compounds CRL 8400 and CRl 8401 are obtained in the form of a brown powder.

4-Methoxy-7H-pyrido[4,3,2-de][1,10]
phenanthroline-7-one (CRL 8400)

Yield: 83% (85 mg).

Melting point: >260° C.

$^1$H NMR (CDCl$_3$): 4.27 (s, 3H); 7.65 (dd, 1H, J=4.8 and 8 Hz); 8.15 (d, 1H, J=6 Hz); 8.70 (s, 1H); 8.78 (dd, 1H, J=8 and 1.9 Hz); 9.10 (d, 1H, J=6 Hz); 9.13 (dd, 1H, J=1.9 and 4.8 Hz).

$^{13}$C NMR (d$_6$-DMSO): 56.97; 115.63; 120.81; 125.52; 129.02; 129.16; 130.22; 136.24; 139.81; 147.37; 149.31; 151.65; 153.07; 154.81; 180.34.

IR (CHCl$_3$): 1674 cm$^{-1}$.

4-Methoxy-7H-pyrido[4,3,2-de][1,7]phenanthroline-7-one (CRL 8401)

Yield: 59%.

Melting point: >260° C.

$^1$H NMR (CDCl$_3$): 4.27 (s, 3H); 7.74 (dd, 1H, J=4.4 and 8.1 Hz); 8.08 (d, 1H, J=5.6 Hz); 8.72 (s, 1H); 8.93 (d, 1H, J=5.6 Hz); 9.05 (dd, 1H, J=1.9 and 4.4 Hz); 9.19 (dd, 1H, J=1.9 and 8.1 Hz).

$^{13}$C NMR (d$_6$-DMSO): 57.03; 115.16; 119.70; 127.69; 129.48; 130.15; 132.86; 133.74; 140.82; 146.80; 147.98; 148.63; 152.81; 152.98; 179.84.

IR (CHCl$_3$): 1679 cm$^{-1}$.

EXAMPLE 7

4,8-Dimethoxy-7H-pyrido[4,3,2-de][1,10]
phenanthroline-7-one (CRL 8803) and 4,11-dimethoxy-7H-pyrido[4,3,2-de][1,7]phenanthroline-7-one (CRL 8440)

A solution of the compound I-9b or of the compound II-9b (100 mg, 0.35 mmol) and of N,N-dimethylformamide diethyl acetal (0.24 ml, 1.23 mmol) in 1 ml of DMF is brought to 120° C. for 90 min. The reaction mixture is concentrated under high vacuum to remove the DMF and the residue is diluted in 100 ml of absolute EtOH. After adding 0.6 g of NH$_4$Cl, the mixture is brought to reflux for 30 min. After concentrating on a rotary evaporator, 30 ml of water are added and the mixture is extracted with CHCl$_3$ (3 times 75 ml). The organic phases are dried over MgSO$_4$ and concentrated. The crude product obtained is purified by flash chromatography through silica (95/5 CHCl$_3$/MeOH) to give the compounds in the form of a yellow powder.

4,11-Dimethoxy-7H-pyrido[4,3,2-de][1,7]
phenanthroline-7-one (CRL 8440)

Yield: 26% (27 mg).

Melting point: >260° C.

$^1$H NMR (d$_6$-DMSO): 4.08 (s, 3H); 4.26 (s, 3H); 7.54 (d, 1H, J=5.9 Hz); 7.98 (d, 1H, 5.9 Hz); 8.77 (d, 1H, J=5.9 Hz); 8.83 (s, 1H); 8.94 (d, 1H, J=5.9 Hz).

$^{13}$C NMR (d$_6$-DMSO): 57.41; 58.07; 112.43; 113.75; 119.84; 122.13; 129.60; 130.54; 140.17; 146.81; 150.17; 150.62; 153.03; 153.35; 166.06; 179.30.

IR (CHCl$_3$): 1682; 1608; 1572 cm$^{-1}$.

MS: m/z 293 (34); 292 (42); 220 (19); 192 (30); 165 (22).

EXAMPLE 8

4-Methoxy-8-dimethylamino-7H-pyrido[4,3,2-de][1,10]phenanthroline-7-one (CRL 8804) and 4-methoxy-11dimethylamino-7H-pyrido[4,3,2-de][1,7]phenanthroline-7-one (CRL 8441)

A solution of the compound I-11b or of the compound II-11b (80 mg, 0.27 mmol) and of N,N-dimethylformamide diethyl acetal (0.18 ml, 0.94 mmol) in 2 ml of DMF is brought to 120° C. for 3 hours. The reaction mixture is concentrated under high vacuum to remove the DMF and the residue is diluted in 90 ml of absolute EtOH. After adding 0.4 g of NH$_4$Cl, the mixture is brought to reflux for 30 min and then concentrated on a rotary evaporator. 30 ml of water are added and then the solution is extracted with CH$_2$Cl$_2$ (3 times 50 ml). The organic phases are dried over MgSO$_4$ and concentrated. The crude product obtained is purified by flash chromatography through silica (95/5 CH$_2$Cl$_2$/MeOH) to give the tetracyclic compounds in the form of a red-brown powder.

4-Methoxy-11-dimethylamino-7H-pyrido[4,3,2-de]
[1,7]phenanthroline-7-one (CRL 8441)

Yield: 40% (33 mg).

Melting point: decomposes.

$^1$H NMR (CDCl$_3$): 3.02 (s, 6H); 4.23 (s, 3H); 7.08 (d, 1H, J=5.9 Hz); 7.87 (d, 1H, J=5.5 Hz); 8.54 (d, 1H, J=5.9 Hz); 8.65 (s, 1H); 8.90 (d, 1H, J=5.5 Hz).

$^{13}$C NMR (CDCl$_3$): 44.28; 56.94; 112.14; 113.63; 119.38; 119.73; 129.31; 129.99; 140.20; 145.81; 150.31; 150.63; 151.41; 152.99; 156.77; 180.57.

IR (CHCl$_3$): 1682 cm$^{-1}$.

MS: m/z 306 (52); 305 (32); 291 (100); 290 (66); 276 (24); 248 (9); 220 (13); 193 (21).

EXAMPLE 9

4,10-Dimethoxy-7H-pyrido[4,3,2-de][1,10]
phenanthroline-7-one (CRL 8805) and 4,9-dimethoxy-7H-pyrido[4,3,2-de][1,7]phenanthroline-7-one (CRL 8479)

A solution of the compound I-12b or of compound II-12b (100 mg, 0.35 mmol) and of N,N-dimethylformamide diethyl acetal (0.24 ml, 1.23 mmol) in 1 ml of DMF is brought to 120° C. for 1 hour. The reaction mixture is concentrated under high vacuum to remove the DMF and the residue is diluted in 100 ml of absolute EtOH. After adding 0.54 g of NH$_4$Cl, the mixture is brought to reflux for 30 min. After concentrating on a rotary evaporator, 20 ml of water are added and the solution is extracted with CHCl$_3$ (3 times 30 ml). The organic phases are dried over MgSO$_4$ and concentrated. The crude product obtained is purified by flash chromatography through silica (CHCl$_3$) to give the tetracyclic compounds in the form of a green powder.

4,9-Dimethoxy-7H-pyrido[4,3,2-de][1,7]
phenanthroline-7-one (CRL 8479)

Yield: 36% (37 mg).

Melting point: >260° C.

$^1$H NMR (d$_6$-DMSO): 4.21 (s, 3H); 4.24 (s, 3H); 7.16 (d, 1H, J=8.8 Hz); 7.98 (d, 1H, 5.6 Hz); 8.69 (s, 1H); 8.85 (d, 1H, J=5.6 Hz); 9.00 (d, 1H, J=8.8 Hz).

$^{13}$C NMR (d$_6$-DMSO): 54.44; 56.92; 114.04; 117.17; 118.86; 127.74; 129.43; 129.99; 136.29; 141.16; 146.36; 146.72; 149.38; 152.94; 165.80; 179.70.

IR (CHCl$_3$): 1679 cm$^{-1}$.

MS: m/z 293 (44); 248 (100); 220 (12).

EXAMPLE 10

9-Ethoxycarbonyl-7H-pyrido[4,3,2-de][1,10]
phenanthroline-7-one (CRL 8805) and 10-ethoxycarbonyl-7H-pyrido[4,3,2-de][1,7]
phenanthroline-7-one (CRL 8482)

A solution of the compound I-13b or of the compound II-13b (30 mg, 0.07 mmol) and of trifluoroacetic acid (0.27 ml, 3.5 mmol) in 15 ml of $CH_2Cl_2$ is stirred for 64 hours. After concentrating on a rotary evaporator, the reaction mixture is basified with 10 ml of saturated $NaHCO_3$ solution and extracted with $CHCl_3$ (2 times 30 ml). The organic phases are dried over $MgSO_4$ and then concentrated on a rotary evaporator. The residue obtained is purified by filtration through silica to give the tetracyclic compounds in the form of a yellow powder.

10-Ethoxycarbonyl-7H-pyrido[4,3,2-de][1,7]phenanthroline-7-one (CRL 8482)

Yield: 53% (11.3 mg).
Melting point: 246° C.
$^1$H NMR ($CDCl_3$): 1.49 (t, 3H, J=7.3 Hz); 4.53 (q, 2H, J=7.3 Hz); 7.85 (d, 1H, J=5.9 Hz); 8.03 (d, 1H, J=5.5 Hz); 8.98 (d, 1H, J=5.9 Hz); 9.22 (d, 1H, J=5.5 Hz); 9.56 (d, 1H, J=1.9 Hz); 9.73 (d, 1H, J=1.9 Hz).
$^{13}$C NMR ($CDCl_3$): 14.32; 62.29; 119.61; 120.39; 124.04; 129.94; 132.60; 135.46; 138.77; 147.78; 149.17; 149.46; 153.23; 164.15; 180.20 (1C not observed).
IR ($CHCl_3$): 1726; 1694 $cm^{-1}$.
MS: m/z 305 (92); 260 (7); 232 (93); 204 (25).

EXAMPLE 11

10-Hydroxy-7H-pyrido[4,3,2-de][1,0]phenanthroline-7-one (CRL 8809) and 9-hydroxy-7H-pyrido[4,3,2-de][1,7]phenanthroline-7-one (CRL 8483)

A solution of the compound I-14b or of the compound II-14b (tricycle 56) (50 mg, 0.135 mmol) and of trifluoroacetic acid (0.54 ml, 7 mmol) in 30 ml of $CH_2Cl_2$ is stirred for 48 hours. After concentrating on a rotary evaporator, the reaction mixture is basified with 13 ml of saturated $NaHCO_3$ solution and extracted with $CH_2Cl_2$ (7 times 30 ml). The organic phases are dried over $MgSO_4$ and then concentrated on a rotary evaporator. The residue obtained is purified by flash chromatography (97/2 $CH_2Cl_2$/MeOH) to give the tetracyclic compounds in the form of an orange powder.

9-Hydroxy-7H-pyrido[4,3,2-de][1,7]phenanthroline-7-one (CRL 8483)

Yield: 50% (16.8 mg).
Melting point: >260° C.
$^1$H NMR ($CDCl_3$): 7.06 (d, 1H, J=9.5 Hz); 7.72 (d, 1H, J=5.9 Hz); 8.02 (d, 1H, J=5.2 Hz); 8.70 (d, 1H, J=9.5 Hz); 8.87 (d, 1H, J=5.9 Hz); 9.19 (d, 1H, J=5.5 Hz).
IR ($CHCl_3$): 1690; 1667; 1602 $cm^{-1}$.
MS: m/z 249 (100); 221 (77.6); 193 (99.2).

EXAMPLE 12

10-Methoxy-7H-pyrido[4,3,2-de][1,10]phenanthroline-7-one (CRL 8810) and 9-methoxy-7H-pyrido[4,3,2-de][1,7]phenanthroline-7-one (CRL 8484)

A solution of the compound I-16b or of the compound II-16b (200 mg, 0.786 mmol) and of N,N-dimethylformamide diethyl acetal (0.47 ml, 2.73 mmol) in 3.2 ml of DMF is brought to reflux for 2 hours. The reaction mixture is concentrated under high vacuum to remove the DMF and the residue is diluted in 200 ml of absolute EtOH. After adding 1.4 g of $NH_4Cl$ (26.2 mmol), the solution is brought to reflux for 30 min. After concentrating on a rotary evaporator, 50 ml of water are added and then the solution is extracted with $CH_2Cl_2$ (5 times 40 ml). The organic phases are dried over $MgSO_4$ and concentrated. The crude product obtained is purified by flash chromatography through silica (99/1 $CH_2Cl_2$/MeOH) to give the tetracyclic compounds in the form of a brown powder.

9-Methoxy-7H-pyrido[4,3,2-de][1,7]phenanthroline-7-one (CRL 8484)

Yield: 10% (20 mg).
Melting point: >260° C.
$^1$H NMR ($CDCl_3$): 4.14 (s, 3H); 7.11 (d, 1H, J=8.8 Hz); 7.63 (d, 1H, J=5.5 Hz); 7.87 (d, 1H, J=5.5 Hz); 8.77 (d, 1H, J=5.5 Hz); 8.91 (d, 1H, J=8.8 Hz); 9.09 (d, 1H, J=5.5 Hz).
$^{13}$C NMR ($CDCl_3$): 53.41; 117.66; 118.54; 118.93; 123.70; 127.73; 136.29; 138.52; 145.95; 147.45; 148.03; 148.83; 150.19; 165.86; 180.55.
IR ($CHCl_3$): 1686 $cm^{-1}$.
MS: m/z 263 (8.2); 233 (25.1); 204 (35.4).

EXAMPLE 13

8,10-Dimethoxy-7H-pyrido[4,3,2-de][1,10]phenanthroline-7-one (CRL 8811) and 9,11-dimethoxy-7H-pyrido[4,3,2-de][1,7]phenanthroline-7-one (CRL 8485)

A solution of the compound I-18b or of the compound II-18b (105 mg, 0.37 mmol) and of N,N-dimethylformamide diethyl acetal (0.22 ml, 1.29 mmol) in 1.5 ml of DMF is brought to reflux for 1 h 30. The reaction mixture is concentrated under high vacuum to remove the DMF and then the residue is diluted in 95 ml of absolute EtOH. 0.7 g of $NH_4Cl$ (13.08 mmol) is added and the solution is brought to reflux for 30 min. After concentrating on a rotary evaporator, 50 ml of water are added. The solution is extracted with $CH_2Cl_2$ (5 times 40 ml). The organic phases are dried over $MgSO_4$ and concentrated. The crude product obtained is purified by flash chromatography through silica (99/1 $CH_2Cl_2$/MeOH) to give the tetracyclic compounds in the form of an orange-yellow powder.

9,11-Dimethoxy-7H-pyrido[4,3,2-de][1,7]phenanthroline-7-one (CRL 8485)

Yield: 9% (10 mg).
Melting point: >260° C.
$^1$H NMR ($CDCl_3$): 4.12 (s, 3H); 4.18 (s, 3H); 6.65 (s, 1H); 7.64 (d, 1H; J=5.5 Hz); 7.92 (d, 1H, J=5.5 Hz); 8.93 (d, 1H, J=5.5 Hz); 9.14 (d, 1H, J=5.5 Hz).
$^{13}$C NMR ($CDCl_3$): 54.39; 57.02; 98.26; 117.89; 118.64; 118.86; 124.16; 138.50; 146.93; 147.09; 148.29; 148.62; 151.50; 166.32; 167.73; 180.65.
IR ($CHCl_3$): 1688 $cm^{-1}$.
MS: m/z 293 (15); 292 (28); 233 (24); 204 (13); 165 (10).

EXAMPLE 14

8-Dimethylamino-10-chloro-7H-pyrido[4,3,2-de][1,7]phenanthroline-7-one (CRL 8812) and 9-chloro-11-dimethylamino-7H-pyrido[4,3,2-de][1,7]phenanthroline-7-one (CRL 8485)

A solution of the compound I-17b or of the compound II-17b (110 mg, 0.375 mmol) and of N,N-dimethylformamide diethyl acetal (0.23 ml, 1.31 mmol) in 1.1 ml of DMF is brought to reflux for 1 h 30. The reaction mixture is concentrated under high vacuum to remove the DMF and then the residue is diluted in 95 ml of absolute EtOH. After adding 0.7 g of NH$_4$Cl (13.08 mmol), the mixture is brought to reflux for 30 min. and then concentrated on a rotary evaporator. 50 ml of water are added and then the solution is extracted with CH$_2$Cl$_2$ (5 times 40 ml). The organic phases are dried over MgSO$_4$ and concentrated. The crude product obtained is purified by flash chromatography through silica (99/1 CH$_2$Cl$_2$/MeOH) to give the tetracyclic compounds in the form of a purple-red powder.

9-Chloro-11-dimethylamino-7H-pyrido[4,3,2-de][1,7]phenanthroline-7-one (CRL 8486)

Yield: 3% (3.3 mg).

Melting point: 246° C.

$^1$H NMR (CDCl$_3$): 3.04 (s, 6H); 7.11 (s, 1H); 7.61 (d, 1H, J=5.5 Hz); 7.92 (d, 1H, J=5.5 Hz); 8.90 (d, 1H, J=5.5 Hz); 9.14 (d, 1H, J=5.5 Hz).

$^{13}$C NMR (CDCl$_3$): 44.39; 113.57; 117.60; 119.00; 119.37; 123.99; 138.50; 146.51; 146.77; 148.83; 150.68; 150.89; 153.68; 158.21; 180.05.

IR (CHCl$_3$): 1698 cm$^{-1}$.

MS: m/z 311 (19); 309 (11); 296 (89); 294 (100); 269 (4); 267 (1); 204 (66).

EXAMPLE 15

4-Hydroxy-7H-pyrido[4,3,2-de][1,10]phenanthroline-7-one dihydroiodide (CRL 8813) and 4-hydroxy-7H-pyrido[4,3,2-de][1,7]phenanthroline-7-one dihydroiodide, (CRL 8487)

Hydriodic acid (57% in water: 10 ml, 44.6 mmol) is added to a suspension of compound CRL 8400 or of compound CRL 8401 (50 mg, 0.19 mmol) in acetic acid (4 ml). The mixture is heated at 100° C. for 21 hours. After cooling and then filtering, the dihydroiodide of the expected compounds is isolated in the form of a purple powder.

4-Hydroxy-7H-pyrido[4,3,2-de][1,7]phenanthroline-7-one dihydroiodide (CRL 8487)

Yield: 85% (82 mg).

Melting point: >260° C.

$^1$H NMR (d$_6$-DMSO): 6.75 (d, 1H, J=5.8 Hz); 7.42 (broad s, 1H); 7.63 (dd, 1H, J=8.4 and 4.4 Hz); 8.20 (d, 1H, J=5.8 Hz); 9.07 (m, 2H).

IR (CHCl$_3$): 3037; 1647; 1635; 1617; 1604 cm$^{-1}$.

EXAMPLE 16

4-Chloro-7H-pyrido[4,3,2-de][1,10]phenanthroline-7-one (CRL 8806) and 4-chloro-7H-pyrido[4,3,2-de][1,7]phenanthroline-7-one (CRL 8480)

A solution of compound CRL 8813 or of compound CRL 8487 (45 mg, 0.14 mmol) in POCl$_3$ (3.5 ml) is brought to reflux for 2 hours. After evaporating on a rotary evaporator, the mixture is basified to pH 8 with a 1N NaHCO$_3$ solution (10 ml) and then extraction is carried out with a 5% MeOH/CHCl$_3$ mixture (2×20 ml). The organic phases are dried over MgSO$_4$ and then concentrated on a rotary evaporator. The residue obtained is purified by flash chromatography (99/1 CH$_2$Cl$_2$/MeOH) to give the expected compounds in the form of a brown powder.

4-Chloro-7H-pyrido[4,3,2-de][1,7]phenanthroline-7-one (CRL 8480)

Yield: 4% (2 mg).

Melting point: >260° C.

$^1$H NMR (CDCl$_3$): 7.78 (dd, 1H, J=4.4 and 8.1 Hz); 8.08 (d, 1H, 5.9 Hz); 9.03 (d, 1H, J=5.9 Hz); 9.07 (dd, 1H, J=4.4 and 1.8 Hz); 9.18 (s, 1H); 9.19 (dd, 1H, J=1.8 and 8.1 Hz).

$^{13}$C NMR (CDCl$_3$): 116.63; 119.80; 128.25; 132.64; 134.05; 137.03; 145.92; 147.56; 147.78 (2C); 148.47; 149.93; 153.31; 180.08.

IR (CHCl$_3$): 1692; 1608 cm$^{-1}$.

MS: m/z 269 (34), 267 (100), 232 (60); 204 (29).

EXAMPLE 17

4-Dimethylamino-7H-pyrido[4,3,2-de][1,10]phenanthroline-7-one (CRL 8807) and 4-dimethylamino-7H-pyrido[4,3,2-de][1,7]phenanthroline-7-one (CRL 8481)

A solution of compound CRL 8806 or of compound CRL 8480 (14 mg, 0.052 mmol) of dimethylamine hydrochloride (24 mg, 0.29 mmol) and of sodium hydroxide (13 mg, 0.32 mmol) in a THF/H$_2$O mixture (2 ml/1 ml) is brought to reflux for 1 h 30. After concentrating on a rotary evaporator, the mixture is taken up in 15 ml of water. After extracting with CHCl$_3$ (3×20 ml), the organic phases are dried over MgSO$_4$ and then concentrated on a rotary evaporator. The residue obtained is purified by flash chromatography (95/5 CHCl$_3$/MeOH) to give the expected compounds in the form of a red powder.

4-Dimethylamino-7H-pyrido[4,3,2-de][1,7]phenanthroline-7-one (CRL 8481)

Yield: 63% (9 mg).

Melting point; >260° C.

$^1$H NMR (CDCl$_3$): 3.34 (s, 6H); 7.71 (dd, 1H, J=4.4 and 8.1 Hz); 7.96 (d, 1H, 6.0 Hz); 8.62 (s, 1H); 8.83 (d, 1H, J=6.0 Hz); 9.04 (dd, 1H, J=1.5 and 4.4 Hz); 9.19 (dd, 1H, J=1.5 and 8.1 Hz).

$^{13}$C NMR (CDCl$_3$): 44.06 (2C); 117.89; 120.40; 127.22; 129.69; 132.59; 133.68; 135.30; 138.51; 144.67; 146.98; 148.14; 149.16; 152.66; 179.55.

IR (CHCl$_3$): 1666 cm$^{-1}$.

MS: m/z 276 (100); 249 (11); 204 (1).

EXAMPLE 18

3-Acetoxymethyl-7H-pyrido[4,3,2-de][1,10]phenanthroline-7-one (CRL 8825) and 3-acetoxymethyl-7H-pyrido[4,3,2-de]]1,7]phenanthroline-7-one (CRL 8824)

A solution of the compound I-1b and of compound II-1b (0.11 g, 0.5 mmol) and of dimethylformamide diethyl acetal (1.5 mmol) in DMF (3 ml) is heated under nitrogen at 120° C. for 1 h. After cooling, the mixture is concentrated under vacuum to produce the expected derivative in the solid form. The preceding solid derivative (125 mg, 0.45 mmol) is taken up in DMF and 13 mg (0.7 mmol) of Eschenmoser's salt is added. The mixture is heated under nitrogen at 115° C. for 30 minutes. After cooling, NH$_4$Cl (10 mmol) and acetic acid (75 ml) are added to the mixture, which is brought to 115° C. for 30 minutes. After cooling, the reaction mixture is poured into ice, basified with 10% KOH and extracted with CHCl$_3$. The organic phases are dried over MgSO$_4$ and concentrated on a rotary evaporator. The residue is purified by flash chromatography through silica.

3-Acetal-7H-pyrido[4,3,2-de][1,10]phenanthroline-7-one (CRL 8815) and 3-acetal-7H-pyrido[4,3,2-de][1,7]phenanthroline-7-one (CRL 8814), 3-cyano-7H-pyrido[4,3,2-de][1,10]phenanthroline-7-one (CRL 8817) and 3-cyano-7H-pyrido[4,3,2-de][1,7] phenanthroline-7-one (CRL 8816), 3-ethoxycarbonyl-7H-pyrido[4,3,2-de][1,10] phenanthroline-7-one (CRL 8819) and 3-ethoxycarbonyl-7H-pyrido[4,3,2-de][1,7]phenanthroline-7-one (CRL 8818)

3-methoxymethyl-7H-pyrido[4,3,2-de][1,10] phenanthroline-7-one (CRL 8821) and 3-methoxymethyl-7H-pyrido[4,3,2-de][1,7]phenanthroline-7-one (CRL 8820)

3-fluoro-7H-pyrido[4,3,2-de][1,10]phenanthroline-7-one (CRL 8823) and 3-fluoro-7H-pyrido[4,3,2-de][1,7] phenanthroline-7-one (CRL 8822)

3-acetoxymethyl-9-methoxy-7H-pyrido[4,3,2-de][1,10] phenanthroline-7-one (CRL 8825) and 3-acetoxymethyl-9-methoxy-7H-pyrido[4,3,2-de][1,7]phenanthroline-7-one (CRL 8824), are prepared according to the procedure described above.

EXAMPLE 19

2-Methyl-7H-pyrido[4,3,2-de][1,10]phenanthroline-7-one (CRL 8827) and 2-methyl-7H-pyrido[4,3,2-de][1,7]phenanthroline-7-one (CRL 8826)

A mixture of compound I-1b and of compound II-b (80 mg, 0.4 mmol) is dissolved in acetic acid (10 ml) with ammonium chloride (64 mg, 12 mmol) and the solution, kept stirred, is heated to 70° C. Acetaldehyde (88 mg, 2 mmol) in acetic acid (10 ml) is added dropwise. The mixture is heated at reflux under nitrogen for 45 minutes and then cooled. After adding water, the solution is basified with $NH_4OH$ and extracted with dichloromethane. After drying on $MgSO_4$ and evaporating, the residue obtained is purified by flash chromatography through silica.

2-Benzyl-7H-pyrido[4,3,2-de][1,10]phenanthroline-7-one (CRL 8829) and 2-benzyl-7H-pyrido[4,3,2-de][1,7] phenanthroline-7-one (CRL 8828), 2-(2'-chloroethyl)-7H-pyrido[4,3,2-de][1,10] phenanthroline-7-one (CRL 8831) and 2-(2'-chloroethyl)-7H-pyrido[4,3,2-de][1,7]phenanthroline-7-one (CRL 8830), 2-(2'-methoxymethyl)-7H-pyrido[4,3,2-de][1,10] phenanthroline-7-one (CRL 8833) and 2-(2'-methoxymethyl)-7H-pyrido[4,3,2-de][1,7]phenanthroline 7-one (CRL 8832), are prepared according to the procedure described above.

The results of the in vitro and in vivo pharmacological tests, presented below, demonstrate the cytotoxic properties of the compounds of formula (I) and (Ia) and the maximum tolerated doses (MTD).

1—Cytotoxic Activity on Tumour Cell Lines in Culture (MTT Test)

The influence of the compounds of formula (I) and of (Ia) on tumour cells was evaluated using the MTT calorimetric test (T. Mosman, J. Immunol. Methods, 1983; 65: 55–63, J. Carmichael et al., Cancer Res. 1987; 47: 936–942).

The principle of the MTT test is based on the mitochondrial reduction by metabolically active alive cells of the yellow-coloured product MTT (3-(4,5-dimethylthiazol-2-yl)-2,5-diphenyltetrazolium bromide) to a blue-coloured product, formazan. The amount of formazan thus obtained is directly proportional to the amount of live cells present in the culture well or wells. This amount of formazan is measured by spectrophotometry.

The cell lines are maintained in monolayer culture at 37° C. in stoppered culture dishes containing 25 MM HEPES MEM (Minimum Essential Medium) base medium. This medium is well suited to the growth of a range of varied diploid or primary mammalian cells. This medium is subsequently supplemented:

with an amount of 5% of FCS (Foetal Calf Serum) decomplemented at 56° C. for 1 hour, with 0.6 mg/ml of L-glutamine, with 200 IU/ml of penicillin, with 200 µg/ml of streptomycin, with 0.1 mg/ml of gentamicin.

The 12 human cancer cell lines which were used were obtained from the American Type Culture Collection (ATCC, Rockville, Md., USA). These 12 cell lines are:

U-373MG (ATCC code: HTB-17) and U-87MG (ATCC code: HTB-14), which are two glioblastomas, SW1088 (ATCC code: HTB-12) which is an astrocytoma, A549 (ATCC code: CCL-185) and A-427 (ATCC code: HTB-53), which are two non-small-cell lung cancers, HCT-15 (ATCC code: CCL-225) and LoVo (ATCC code: CCL-229), which are two colorectal cancers, T-47D (ATCC code: HTB-133) and MCF7 (ATCC code: HTB-22), which are two breast cancers, J82 (ATCC code: HTB-1) and T24 (ATCC code: HPB-4), which are two bladder cancers, PC-3 (ATCC code: CRL-1435), which is a prostate cancer.

Experimentally: 100 µl of a cell suspension comprising 20 000 to 50 000 (depending on the cell type used) cells/ml of culture medium are inoculated in flat-bottomed 96-well multi-well plates and are incubated at 37° C. under an atmosphere comprising 5% of $CO_2$ and 70% humidity. After incubating for 24 hours, the culture medium is replaced with 100 µl of fresh medium comprising either the various test compounds at concentrations varying from $10^{-5}$ to $10^{-10}$ M of the solvent used to dissolve the -test products (control condition). After incubating for 72 hours under the above conditions, the culture medium is replaced with 100 µl of a yellowish solution of MTT dissolved, in a proportion of 1 mg/ml, in RPMI 1640. The microplates are reincubated for 3 hours at 37° C. and then centrifuged for 10 minutes at 400 g. The yellowish MTT solution is removed and the blue formazan crystals formed at the cellular level are dissolved in 100 µl of DMSO. The microplates are subsequently agitated for 5 minutes. The intensity of the resulting blue coloration, and thus of the conversion of the yellow MTT product into blue formazan by the cells which are still alive at the end of the experiment, is quantified by spectrophotometry using a device of DYNATECH IMOASSAY SYSTEM type at wavelengths of 570 nm and 630 nm corresponding respectively to the maximum absorption wavelengths of formazan and to the background noise. Software built into the spectrophotometer calculates the mean optical density values and the standard deviation (Std. Dev.) and standard error of the mean (SEM) values.

The inhibitory activity on the cell growth of the compounds of formula (I) and (Ia) on the various tumour cell lines was measured in comparison with that of the natural product. By way of example, the values of the concentrations framing the 50% inhibitory concentrations ($IC_{50}$) obtained for each compound are presented in Table I below:

All of the compounds studied exhibit significant inhibitory activity on the cell proliferation of the 12 human tumour lines: U-87MG, U-373MG, SW1088, T24, J82, HCT-15, LoVo, MCF7, T-47D, A549, A-427 and PC-3, with an $IC_{50}$ which can be between $10^{-5}$ and $10^{-9}$ M, depending on the compounds and the tumour lines tested.

2—Determination of the Maximum Tolerated Dose (MTD)

The evaluation of the maximum tolerated dose was carried out on B6D2F1/Jico mice aged from 4 to 6 weeks. The compounds were administered intraperitoneally at increasing doses ranging from 2.5 to 160 mg/kg. The value of the MTD (expressed in mg/kg) is determined from the observation of the survival rates of the animals over a period of 14 days after a single administration of the product under consideration. The change in the weight of the animals is also monitored over this period. When that the value of the MTD is greater than 160 mg/kg, the value of the MTD is categorized as 160 mg/kg by default.

The results of the assessment of the maximum tolerated dose (MTD) are collated in the following Table II:

TABLE 2

Maximum Tolerated Doses

| CRL Compounds | DMT (mg/kg) |
| --- | --- |
| CRL 8388 (Example 4) | 10 |
| CRL 8293 (Example 1) | 10 |
| CRL 8294 (Example 1) | 10 |
| CRL 8363 (Example 2) | 10 |
| CRL 8364 (Example 2) | 5 |
| CRL 8367 (Example 3) | 10 |
| CRL 8396 (Example 5) | 20 |
| CRL 8400 (Example 6) | >160 |
| CRL 8401 (Example 6) | >160 |
| CRL 8440 (Example 7) | 20 |
| CRL 8441 (Example 8) | >160 |

The products of this family exhibit either a degree of direct toxicity or may be devoid of it and may then be used in vivo at high tissue concentrations and therefore at high dosages.

3—In Vivo Antitumour Activity

The tests were carried out on models of:
hormone-insensitive mouse mammary carcinoma MXT (HI-MXT),
hormone-sensitive mouse mammary adenocarcinoma MXT (HS-MXT),
lymphoma L 1210.

The model of mouse mammary adenocarcinoma MXT of Watson C. et al. (Cancer Res., 1977; 3–7: 3344-48), grafted onto B6D2F1/Jico mice aged from 4 to 6 weeks, is derived from the mammary gland milk ducts. Initially hormone-sensitive (HS-MXT model), the differentiated tumour develops in the direction of an undifferentiated hormone-insensitive tumour (HI-MXT model). The agents with the antitumour activity which has been demonstrated clinically prolong the survival of the animals carrying HI-MXT tumours and HS-MXT tumours. This is the case, for example, with cyclophosphamide, etoposide or adriamycin.

The model of lymophoma L 1210 is a model of L 1210 leukemia cells of mouse origin grafted subcutaneously in the mouse. They give rise, in 100% of cases, to a rapid-growth subcutaneous solid tumour (L 1210 s.c.).

When the MTD value of a product was determined, its in vivo antitumour activity was characterized at the MTD/2, MTD/4 and MTD/8 doses on the models of mammary adenocarcinoma of mouse origin HS-MXT and of mouse mammary carcinoma HI-MXT and on the model of subcutaneous lymphoma L 1210.

In all the examples presented below, whatever the model, the control condition is represented by a batch of 9 or 15 mice to which is administered, for 3 consecutive weeks and at the rate of 3 administrations (Monday, Wednesday and Friday) per week, a volume of 0.2 ml of physiological saline comprising the solvent used to dissolve the various compounds of formula (I) and (Ia) used.

During these tests, either the tumour growth or the survival rate of the mice were determined:

i)—The tumour growth was evaluated by measuring twice weekly (Monday and Friday) the area of the grafted HS-MXT, HI-MXT or L 1210 tumours. This area is calculated by multiplying the value of the two greatest perpendicular axes of the tumour. The value of these axes is measured using a sliding caliper.

ii)—The survival rate of the mice is calculated in the form or a ratio T/C, where:

$$T = \frac{\text{(Number of days of survival of the median mouse of the batch of mice treated)} + \text{(Median mouse treated)} \times \text{(Number of dead mice in the days which preceded that of the median mouse treated)}}{\text{(Number of dead mice on the same day as the median mouse treated)}}$$

$$C = \frac{\text{(Number of days of survival of the median mouse of the batch of mice treated)} + \text{(Median mouse)} \times \text{(Number of dead mice in the days which preceded that of the median mouse treated)}}{\text{(Number of dead mice on the same day as the median mouse)}}$$

This ratio represents the mean survival time of the mean mouse of the batch of treated mice with respect to the mean survival time of the median mouse of the batch of control mice. Thus, a molecule induces a significant ($P<0.05$) increase in the survival of the animals when the T/C index exceeds 130%. On the other hand, it has a toxic effect when this T/C value is less than 70%.

3.1.—Mouse Mammary Carcinoma (HI-MXT)

The influence of the two products CRL 8293 and CRL 8294 on the growth of HI-MXT tumours will be presented below by way of example. Each batch of mice grafted with HI-MXT tumours relating to a given experimental condition comprises 15 animals.

Treatment 1

The product CRL 8293 is administered intraperitoneally. The first injection of the product is carried out on the seventh day postgrafting (D7) at the rate of the seventh day postgrafting (D7) at the rate of 3 injections per week (Monday, Wednesday and Friday) for 3 consecutive weeks and at a dose of 5 mg/kg.

Treatment 2

The product CRL 8294 is administered intraperitoneally. The first injection of the product is carried out on the seventh day postgrafting (D7) at the rate of 3 injections per week (Monday, Wednesday and Friday) for 3 consecutive weeks and at a dose of 5 mg/kg.

The decreases (−) or the increases (+) in the area of the HI-MXT tumours induced with treatments 1 and 2 with respect to the control condition on the 21st day after the tumour grafting, i.e. after 6 administrations of the product CRL 8293 or of the product CRL 8294, are shown, as percentage, in the following Table II. 100% of the control animals are still alive on the 21st day postgrafting.

TABLE III

| Treatments | Tumour area (expressed as %) |
|---|---|
| 1 (CRL 8293) | −33 |
| 2 (CRL 8294) | −36 |

These results show that these two products CRL 8293 and CRL 8294 induce a significant decrease in the growth of the HI-MXT tumours. These results show that these products of formula I and Ia exhibit, in vivo and on this model, an advantageous antitumour activity.

3.2.—Mouse Mammary Adenocarcinoma (HS-MXT)

The influence of the two products CRL 8293 and CRL 8294 on the growth of HS-MXT tumours will be presented below by way of example. Each batch of mice grafted with the HS-MXT tumours relating to a given experimental condition comprises 9 animals.

Treatment 10

The product CRL 8293 is administered intraperitoneally. The first injection of the product is carried out on the seventh day postgrafting (D7) at the rate of 3 injections per week (Monday, Wednesday and Friday) for 3 consecutive weeks and at a dose of 5 mg/kg.

Treatment 20

The product CRL 8294 is administered alone by the intraperitoneal route. The first injection of the product is carried out on the seventh day postgrafting (D7) at the rate of 3 injections per week (Monday, Wednesday and Friday) for 3 consecutive weeks and at a dose of 5 mg/kg.

The decreases (−) or the increases (+) in the area of the HS-MXT tumours induced with treatments 10 and 20 with respect to the control condition on the 31st day after the tumour grafting, i.e. after the 9 administrations provided in the experimental protocol of the 2 products CRL 8293 and CRL 8294, are shown, as percentage, in the following Table IV. 100% of the control animals are still alive on the 31st day postgrafting.

TABLE IV

| Treatments | Tumour area (expressed as %) |
|---|---|
| 10 (CRL 8293) | −45 |
| 20 (CRL 8294) | −64 |

These results show that these two products CRL 8293 and CRL 8294 induce a very highly significant decrease in the growth of the HS-MXT tumours. These results show, as on the HI-MXT model, that the products of formula I and Ia also exhibit on the HS-MXT model a highly advantageous antitumour activity.

3.3.—Lymphoma L 1210

The influence of CRL 8294 on the survival time of the mice will be presented below by way of example (Table V). Each batch of mice grafted with the lymphoma L 1210 relating to a given experimental condition comprises 9 animals.

Treatment 100

The product CRL 8294 is administered alone intraperitoneally. The first injection of the product is carried out on the seventh day postgrafting (D7) at the rate of 3 injections per week (Monday, Wednesday and Friday) for 3 consecutive weeks and at a dose of 1.25 mg/kg.

TABLE V

| Treatment | T/C (expressed a %) |
|---|---|
| 100 (CRL 8294) | 136 |

The compound CRL 8294 of formula (I) exhibits an antitumour activity on the model of subcutaneous lymphoma L 1210. This activity is characterized by a significant extension of the mean survival time of the median mouse of the batch of mice thus treated with respect to the mean survival time of the median mouse of the batch of control mice.

4—Tolerance/cytotoxic activity ratios

The results of the mean $IC_{50}$ values (in nM) (calculated from the individual cytotoxic activities obtained on each of the 12 tumour lines studied) and the $MTD/IC_{50}$ ratios, calculated by taking the ratio of the MTD values to the $IC_{50}$ values, are presented in the following Table VI. The $MTD/IC_{50}$ ratio is expressed as a dimensionless number.

TABLE VI

| CRL Compounds | $IC_{50}$ (nM) | $MTD/IC_{50}$ | $MTD/IC_{50}$* |
|---|---|---|---|
| CRL 8388 (Example 4) | 6200 | 0.0016 | 1 |
| CRL 8293 (Example 1) | 1250 | 0.008 | 5 |
| CRL 8294 (Example 1) | 1450 | 0.007 | 4.4 |
| CRL 8363 (Example 2) | 500 | 0.02 | 12.5 |
| CRL 8364 (Example 2) | 270 | 0.019 | 12 |
| CRL 8367 (Example 3) | 1650 | 0.006 | 3.8 |
| CRL 8396 (Example 5) | 600 | 0.033 | 20.6 |
| CRL 8400 (Example 6) | 380 | 0.42 | 262 |
| CRL 8401 (Example 6) | 53 | 3 | 1870 |
| CRL 8440 (Example 7) | 10 | 0.42 | 1240 |
| CRL 8441 (Example 8) | 5000 | 3 | 19.8 |

*the $MTD/IC_{50}$ ratio of the various compounds was evaluated by taking, as reference, a ratio equal to 1 for CRL 8388.

The compounds of formula (I) and (Ia) exhibit significant antitumour activity both in vitro and in vivo under the experimental conditions described above. They inhibit, in vitro, the growth of tumour cells, as indicated by the results of the MTT calorimetric tests. They significantly and greatly inhibit, in vivo, the growth of HI-MXT and HS-MXT tumours and significantly increase the mean survival time of the median mouse of the batch of mice thus treated and grafted with lymphoma L 1210 with respect to the mean survival time of the median mouse of the batch of control mice.

By virtue of their cytotoxic properties, the compounds of formulae (I) and (Ia), as described or in the form of acceptable pharmaceutical salts or solvates, can be used as active principles of medicaments for treating cancerous tumours and their metastases.

The compounds of formulae (I) and (Ia) are generally administered in dosage units drawn up either per $m^2$ of body surface or per kg of weight. The said dosage units are preferably formulated in pharmaceutical compositions in which the active principle is mixed with one (or more) pharmaceutical excipient(s).

The compounds of formula (I) and (Ia) can be used, according to the cancer pathology of the subject to be treated, at doses of between 0.05 and 350 mg/$m^2$ of body surface, preferably at doses of 0.5 to 50 mg/$m^2$/day for the curative treatment in its acute phase, as a function of the number of treatment cycles of each cure. For a maintenance treatment, the compounds of formulae (I) and (Ia) will advantageously be used at doses of 0.05 to 25 mg/$m^2$/day, preferably at doses of 0.1 to 1.5 mg/$m^2$/day, according to the number of treatment cycles of the cure. They may be used in combination with antitumour medicaments used in protocols validated for intensive polychemotherapy.

In the pharmaceutical compositions of the present invention for oral or intravenous administration, the active principles can be administered in unit administration forms, as a mixture with conventional pharmaceutical vehicles suitable for human therapeutics. The appropriate unit administration forms comprise forms to be taken orally, such as tablets, which may optionally be scored, or gelatin capsules, implants and intravenous administration forms.

For parenteral administration (intravenous infusion at a constant flow rate), use is made of sterile aqueous suspensions, sterile isotonic saline solutions or sterile and injectable solutions which comprise pharmacologically compatible dispersing agents and/or solubilizing agents, for example propylene glycol, polyethylene glycol or a β-cyclodextrin.

Thus, to prepare an aqueous solution for intravenous injection intended for an infusion carried out over 1 to 24 h, use may be made of a cosolvent: an alcohol, such as ethanol, or a glycol, such as polyethylene glycol or propylene glycol, and a hydrophilic surfactant, such as Tween 80.

When a solid composition in the form of tablets is prepared, a wetting agent, such as sodium lauryl sulphate, can be added to the micronized or unmicronized active principle, and the entire combination is mixed with a pharmaceutical vehicle, such as silica, gelatin, starch, lactose, magnesium stearate, talc, gum arabic or the like. The tablets can be coated with sucrose, with various polymers or with other appropriate materials while alternatively they can be treated so that they have a sustained or delayed activity and so that they continuously release a predetermined amount of active principle.

The preparation as gelatin capsules is obtained by mixing the active principle with a diluent, such as a glycol or a glycerol ester, and incorporating the mixture obtained in soft or hard gelatin capsules.

The active principle can also be formulated in the form of microcapsules or microspheres, optionally with one or more supports or additives.

The active principle can also be presented in the form of a complex with a cyclodextrin, for example α-, β- or γ-cyclodextrin, 2-hydroxypropyl-β-cyclodextrin or methyl-β-cyclodextrin.

The compound of formulae (I) and (Ia) will be used in the treatment of the majority of solid tumours as a result of their powerful cytotoxic activities, in particular for treating cerebral tumours, lung cancers, ovarian and breast tumours, endometrium cancers, colorectal cancers, prostate cancers and testicular tumours.

What is claimed is:
1. Compounds of formulae:

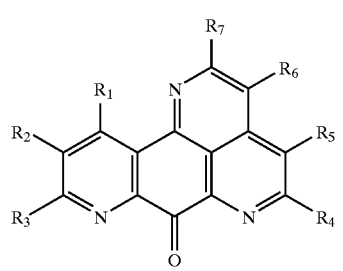

Formula I and

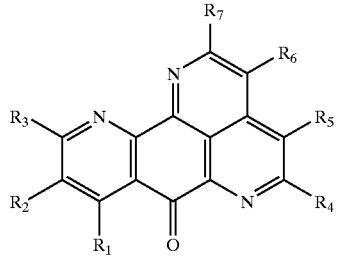

Formula Ia in which:
$R_1$, $R_2$, $R_3$, $R_4$ and $R_5$ are selected from hydrogen, halogens, $C_1$–$C_6$ alkyl groups, hydroxyl, —CHO, —$OR_8$, —COOH, —CN, —$CO_2R_8$, —$CONHR_8$, —$CONR_8R_9$, —$NH_2$, —$NHR_8$, —$N(R_8)_2$, —NH—$CH_2$—$CH_2$—$N(CH_3)_2$, —NH—$CH_2$—$CH_2$—Cl, —$NHCOR_8$, morpholino, nitro, $SO_3H$,

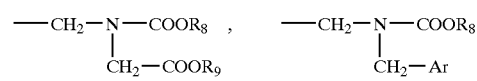

$R_8$ and $R_9$ being selected from $C_1$–$C_6$ alkyl groups and phenyl($C_1$–$C_4$)alkyl groups and Ar being a $C_6$–$C_{14}$ aryl group, $R_6$ is selected from hydrogen, halogens, $C_1$–$C_6$ alkyl or —$(CH_2)_nR_{10}$ groups with $R_{10}$ being selected from halogens or —OH, (C1–C6)alkoxy or —O—CO—($C_1$–$C_6$)alkyl groups and n between 1 and 6, —CN, —$CO_2$Et or —$COR_{11}$ groups with $R_{11}$ being selected from $C_1$–$C_6$ and phenyl($C_1$–$C_4$)alkyl groups, and —$NR_{12}R_{13}$ groups with $R_{12}$ and $R_{13}$ selected, independently of one another, from hydrogen or $C_1$–$C_6$ alkyl, phenyl($C_1$–$C_4$)alkyl or —$(CH_2)_n$ $R_{14}$ groups with $R_{14}$ being selected from halogens or ($C_1$–$C_6$)alkoxy and —$N(CH_3)_2$ groups and n between 1 and 6, $R_7$ is selected from hydrogen, ($C_1$–$C_6$)alkyl, phenyl ($C_1$–$C_4$)alkyl, —$NR_{15}R_{16}$ with $R_{15}$ and $R_{16}$ selected, independently of one another, from hydrogen, $C_1$–$C_6$ alkyl and phenyl($C_1$–$C_4$)alkyl and —$(CH_2)_nR_{17}$, with $R_{17}$ selected from hydrogen, halogens or —OH or ($C_1$–$C_6$)alkoxy groups and n between 1 and 6, and the addition salts of these compounds with pharmaceutically acceptable acids.

2. Compounds according to claim 1, which are compounds of formulae I or Ia in which:
$R_1$, $R_2$, $R_3$, $R_4$ and $R_5$ are selected from hydrogen, halogens, $C_1$–$C_6$ alkyl groups, hydroxyl, —CHO, —$OR_8$, —COOH, —CN, —$CO_2R_8$, —$CONHR_8$, —$CONR_8R_9$, —$NH_2$, —$NHR_8$, —$N(R_8)_2$, —NH—$CH_2$—$CH_2$—$N(CH_3)_2$, —$NHCOR_8$, morpholino, nitro, $SO_3H$,

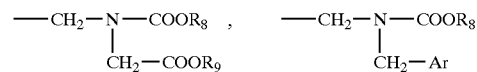

$R_8$ and $R_9$ being selected from $C_1$–$C_6$ alkyl groups and Ar being a $C_6$–$C_{14}$ aryl group.

3. Compounds according to claim 1, which are compounds of formulae I or Ia in which:
$R_1$, $R_2$, $R_3$, $R_4$ and $R_5$ are selected from hydrogen, halogens, $C_1$–$C_6$ alkyl groups, hydroxyl, —$OR_8$, $NO_2$, —NH$_2$, —NHR$_8$, —NH(R$_8$)$_2$, —NH—CH$_2$—CH$_2$—N(CH$_3$)$_2$, —NH—CH$_2$CH$_2$—Cl, —NHCOR$_8$, R$_8$ being selected from C$_1$–C$_6$ alkyl groups, R$_6$ is selected from hydrogen, —(CH$_2$)$_n$R$_{10}$ groups, with R$_{10}$ being selected from halogens, the —O—CO—CH$_3$ group, C$_1$–C$_6$ alkyl groups and NR$_{12}$R$_{13}$ groups with R$_{12}$ and R$_{13}$ selected, independently of one another, from hydrogen or C$_1$–C$_6$ alkyl, benzyl or —(CH$_2$)$_n$R$_{14}$ groups, with R$_{14}$ being selected from halogens or (C$_1$–C$_6$)alkoxy and —N(CH$_3$)$_2$ groups and n between 1 and 6, R$_7$ selected from hydrogen or (C$_1$–C$_6$)alkyl, benzyl, —NR$_{15}$R$_{16}$ with R$_{15}$ and R$_{16}$ selected from hydrogen, C$_1$–C$_6$ alkyl and benzyl, and —(CH$_2$)$_n$R$_{17}$, with R$_{17}$ selected from hydrogen, halogens or —OH or (C$_1$–C$_6$)alkoxy groups and n between 1 and 6, and the addition of salts of these compounds with pharmaceutically acceptable acids.

4. Compounds according to claim 3, which are compounds of formulae I or Ia in which at least one of the R$_1$, R$_2$, R$_3$, R$_4$ and R$_5$ groups is an OR$_8$ group.

5. Compounds according to claim 3, which are compounds of formulae I or Ia in which:

R$_1$ is selected from hydrogen, halogens or hydroxyl, methoxy, nitro, —NH$_2$, —NHCH$_3$, —NH—CH$_2$—CH$_2$—N(CH$_3$)$_2$, —NH—CH$_2$—CH$_2$—Cl or —NHCOCH$_3$ groups, R$_2$ is hydrogen, R$_3$ and R$_5$ are selected from hydrogen or hydroxyl or methoxy groups and the addition salts of these compounds with pharmaceutically acceptable acids.

6. Compounds according to claim 3, which are compounds of formula (I):

11-methoxy-7H-pyrido[4,3,2-de][1,7]phenanthroline-7-one, 11-chloro-7H-pyrido[4,3,2-de][1,7]phenanthroline-7-one, 4-methoxy-7H-pyrido[4,3,2-de][1,7]phenanthroline-7-one, 4,11-dimethoxy-7H-pyrido[4,3,2-de][1,7]-phenanthroline-7-one, 4,9-dimethoxy-7H-pyrido[4,3,2-de][1,7]-phenanthroline-7-one, 9-methoxy-7H-pyrido[4,3,2-de][1,7]phenanthroline-7-one, 9,11-dimethoxy-7H-pyrido[4,3,2-de][1,7]-phenanthroline-7-one, 3-acetoxymethyl-7H-pyrido[4,3,2-de][1,7]phenanthroline-7-one, 3-acetoxymethyl-9-methoxy-7H-pyrido[4,3,2-de][1,7]phenanthroline-7-one, 2-(2-chloroethyl)-7H-pyrido[4,3,2-de][1,7]phenanthroline-7-one, and the addition salts of these compounds with pharmaceutically acceptable acids.

7. Compounds according to claim 3, which are compounds of formula (Ia):

8-methoxy-7H-pyrido[4,3,2-de][1,10]phenanthroline-7-one, 8-chloro-7H-pyrido[4,3,2-de][1,10]phenanthroline-7-one, 4-methoxy-7H-pyrido[4,3,2-de][1,10]phenanthroline-7-one, 4,8-dimethoxy-7H-pyrido[4,3,2-de][1,10]-phenanthroline-7-one, 4,10-dimethoxy-7H-pyrido[4,3,2-de][1,10]phenanthroline-7-one, 10-methoxy-7H-pyrido[4,3,2-de][1,10]-phenanthroline-7-one, 8,10-dimethoxy-7H-pyrido[4,3,2-de][1,10]phenanthroline-7-one, 3-acetoxymethyl-7H-pyrido[4,3,2-de][1,10]phenanthroline-7-one, 3-acetoxymethyl-9-methoxy-7H-pyrido[4,3,2-de][1,10]phenanthroline-7-one, 2-(2-chloroethyl)-7H-pyrido[4,3,2-de][1,10]phenanthroline-7-one, and the addition salts of these compounds with pharmaceutically acceptable acids.

8. Pharmaceutical composition comprising an effective amount of a compound selected from the compounds according to claim 1 for treating, by virtue of their cytotoxic properties, cancerous tumours and their metastases.

9. Process for the preparation of compounds according to claim 1, which consists in:

a) reacting, according to a hetero Diels-Alder reaction, a quinolinedione of formula:

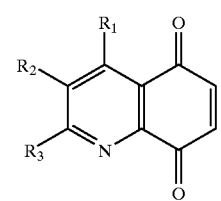

IV and an azadiene of formula

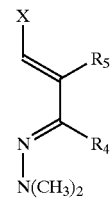

V where X=CH$_3$, in order to obtain a mixture of compounds

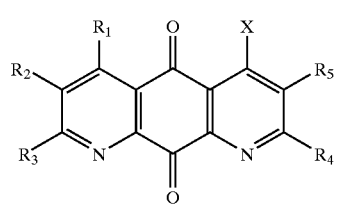

Formula II

+

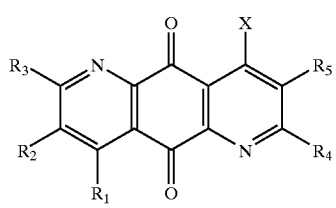

Formula IIa b) optionally separating the compounds of formulae II and IIa, $c_1$) subsequently reacting a compound of formulae II and or IIa with dimethylformamide dimethyl acetal, in order to obtain an enamine of formula:

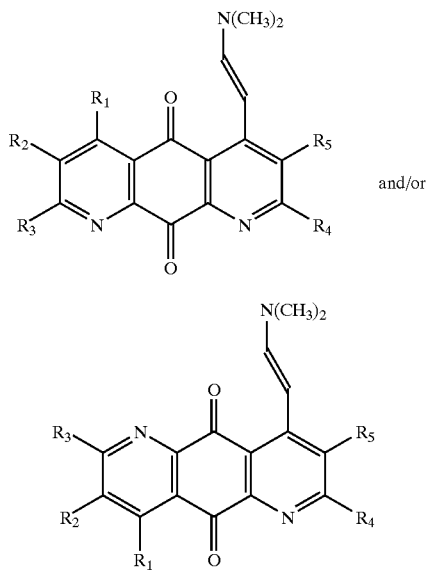

Formula III and/or

Formula IIIa then functionalizing the enamines, in order to introduce the $R_6$ and/or $R_7$ substituents, and cyclizing, in order to obtain the compounds of formulae I and/or Ia, or $c_2$) functionalizing and cyclizing at the same time, in order to obtain the compounds of formulae I and/or Ia, d) optionally separating the compounds of formulae I and Ia.

10. Process for the preparation of compounds according to claim 1 of formulae I or Ia in which and $R_7$ are hydrogen atoms, which consists:

a) in reacting, according to a hetero Diels-Alder reaction, a quinolinedione of formula:

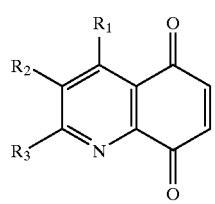

IV and an azadiene of formula

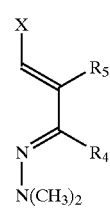

V where $X=CH_2-CH_2-NHBoc$, wherein Boc corresponds to tert-butoxycarbonyl, in order to obtain a mixture of compounds

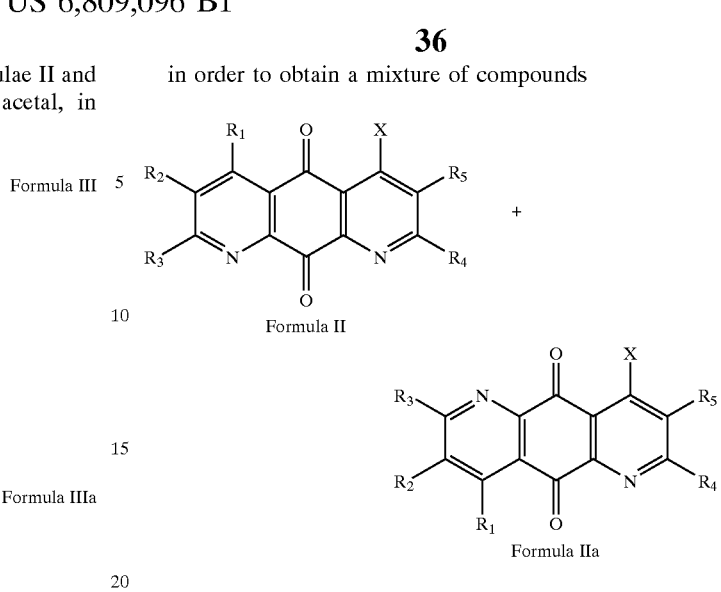

Formula II

+

Formula IIa b) optionally separating the compounds of formulae II and IIa, c) cyclizing a compound of formulae II and/or IIa, in order to obtain a compound of formulae I and/or Ia, d) optionally separating the compounds of formulae I or Ia.

11. Enamine of formula:

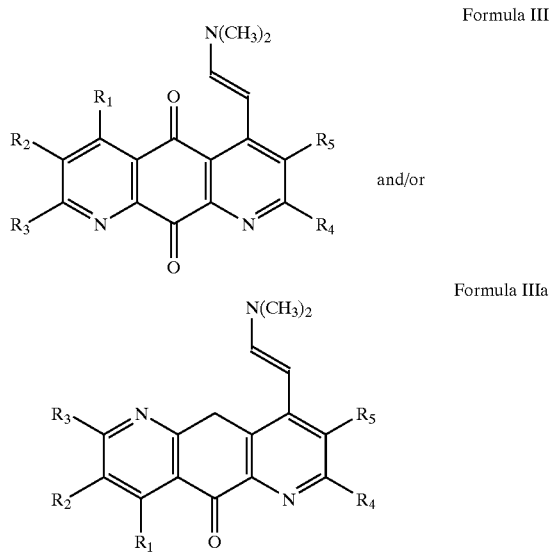

Formula III and/or

Formula IIIa in which:

$R_1$, $R_2$, $R_3$, $R_4$ and $R_5$ are selected from hydrogen, halogens, $C_1$–$C_6$ alkyl groups, hydroxyl, —CHO, —$OR_8$, —COOH, —CN, —$CO_2R_8$, —$CONHR_8$, —$CONR_8R_9$, —$NH_2$, —$NHR_8$, —$N(R_8)_2$, —NH—$CH_2$—$CH_2$—$N(CH_3)_2$, —NH—$CH_2$—$CH_2$—Cl, —$NHCOR_8$, morpholino, nitro, $SO_3H$, $$-CH_2-N-COOR_8 \quad , \quad -CH_2-N-COOR_8$$
$$\quad\quad\quad | \quad\quad\quad\quad\quad\quad\quad\quad\quad | $$
$$\quad\quad\quad CH_2-COOR_9 \quad\quad\quad\quad CH_2-Ar$$

$R_8$ and $R_9$ being selected from $C_1$–$C_6$ alkyl groups and phenyl($C_1$–$C_4$)alkyl groups and Ar being a $C_6$–$C_{14}$ aryl group.

12. A method for treating a solid tumour in a patient, which consists in administering, to said patient, an effective amount of a compound according to claim 1, and wherein said solid tumour are selected from the group consisting of cerebral tumours, lung cancers, ovarian tumours, breast tumours, endometrium cancers, colorectal cancers, prostate cancers, testicular tumours, glioblastomas, astrocytomas, non-small-cell lung cancers, bladder cancers, carcinomas and adeno carcinomas.

13. A method for treating a solid tumour in a patient, comprising administering to said patient an effective amount of a compound according to claim 1, and wherein said solid tumour is selected from the group consisting of cerebral tumours, lung cancers, ovarian tumours, breast tumours, endometrium cancers, colorectal cancers, prostate cancers, testicular tumours, glioblastomas, astrocytomas, non-cell-lung cancers, bladder cancers, carcinomas and adeno carcinomas.

\* \* \* \* \*